(12) United States Patent
Buechler et al.

(10) Patent No.: US 7,379,964 B1
(45) Date of Patent: May 27, 2008

(54) METHOD OF FACILITATING MEDICAL CONSULTATIONS

(75) Inventors: James R. Buechler, Terre Haute, IN (US); Evan Farmer, Norfolk, VA (US); Todd J. Smaka, Indianapolis, IN (US)

(73) Assignee: Union Hospital, Inc., Terre Haute, IN (US)

( * ) Notice: Subject to any disclaimer, the term of this patent is extended or adjusted under 35 U.S.C. 154(b) by 818 days.

(21) Appl. No.: 10/039,584

(22) Filed: Oct. 26, 2001

Related U.S. Application Data

(60) Provisional application No. 60/243,374, filed on Oct. 26, 2000.

(51) Int. Cl.
*G06F 15/16* (2006.01)
*G06F 17/60* (2006.01)

(52) U.S. Cl. .................... 709/203; 434/236; 434/238

(58) Field of Classification Search ............. 709/201, 709/217, 218, 219, 202–205; 600/300, 30; 128/904, 903; 705/1, 2–4, 17, 25, 26; 707/1, 707/3, 2, 9, 10; 434/236, 238
See application file for complete search history.

(56) References Cited

U.S. PATENT DOCUMENTS

| | | | |
|---|---|---|---|
| 5,307,263 A | 4/1994 | Brown | |
| 5,390,238 A | 2/1995 | Kirk et al. | |
| 5,441,047 A | 8/1995 | David et al. | |
| 5,619,991 A * | 4/1997 | Sloane | 600/300 |
| 5,664,109 A * | 9/1997 | Johnson et al. | 705/2 |
| 5,779,634 A | 7/1998 | Ema et al. | |
| 5,802,494 A | 9/1998 | Kuno | |
| 5,822,715 A | 10/1998 | Worthington et al. | |
| 5,855,550 A | 1/1999 | Lai et al. | |
| 5,897,493 A | 4/1999 | Brown | |
| 5,899,855 A | 5/1999 | Brown | |
| 5,911,132 A | 6/1999 | Sloane | |
| 5,911,687 A | 6/1999 | Sato et al. | |
| 5,951,469 A | 9/1999 | Yamaura | |
| 5,960,085 A * | 9/1999 | de la Huerga | 340/5.61 |
| 5,989,187 A | 11/1999 | Clawson | |
| 5,997,476 A | 12/1999 | Brown | |
| 6,014,432 A | 1/2000 | Modney | |
| 6,022,315 A | 2/2000 | Iliff | |
| 6,024,699 A | 2/2000 | Surwit et al. | |
| 6,168,563 B1 | 1/2001 | Brown | |
| 6,184,030 B1 * | 2/2001 | Katoot et al. | 435/287.2 |
| 6,190,313 B1 * | 2/2001 | Hinkle | 600/300 |
| 6,270,455 B1 * | 8/2001 | Brown | 600/300 |
| 6,272,470 B1 * | 8/2001 | Teshima | 705/3 |
| 6,283,761 B1 * | 9/2001 | Joao | 434/236 |
| 6,321,203 B1 * | 11/2001 | Kameda | 705/3 |
| 6,347,329 B1 * | 2/2002 | Evans | 709/202 |

(Continued)

OTHER PUBLICATIONS

"AskJeeves", Waybackmachine, Mar. 4, 2000, www.ask.com.*

*Primary Examiner*—David Wiley
*Assistant Examiner*—Jude J Jean-Gilles
(74) *Attorney, Agent, or Firm*—Barnes & Thornburg LLP

(57) ABSTRACT

A method for a first healthcare provider to consult a second healthcare provider regarding at least one of diagnosis of a patient and treatment of a patient includes the first healthcare provider submitting a request for consultation on a machine, and the second healthcare provider submitting a consultation response on a machine.

22 Claims, 39 Drawing Sheets

U.S. PATENT DOCUMENTS

| | | |
|---|---|---|
| 6,757,898 B1 * | 6/2004 | Ilsen et al. .................. 709/203 |
| 7,028,049 B1 * | 4/2006 | Shelton ................... 707/104.1 |
| 2001/0037219 A1 * | 11/2001 | Malik ............................ 705/2 |
| 2001/0037334 A1 * | 11/2001 | Valentine ..................... 707/10 |
| 2001/0051881 A1 * | 12/2001 | Filler ............................ 705/3 |
| 2002/0010679 A1 * | 1/2002 | Felsher ........................ 705/51 |
| 2002/0022973 A1 * | 2/2002 | Sun et al. ..................... 705/3 |
| 2002/0055176 A1 * | 5/2002 | Ray ............................ 436/67 |
| 2004/0117215 A1 * | 6/2004 | Marchosky .................... 705/3 |
| 2005/0187796 A1 * | 8/2005 | Rosenfeld et al. ............. 705/3 |

* cited by examiner

Screenshot of Netscape browser window titled "Case Data – Netscape" showing a RuralConsult web page.

Location: https://www.ruralconsult.com/SecurePages/CME/DermaCase.asp

Currently on cephalexin 500mg bid.

reason for consult
Severity of the lesions is very worrisome considering no other suspected or diagnosed complicating factors — 515 assessment/diagnosis — 516
Most likely this represents a bacterial infection, either a folliculitis or secondary to insect bites.

differential diagnosis — 517
Sweet's disease (acute febrile neutrophilic dermatosis).
Pyoderma gangrenosum
Fungal infection
Mycobacterial infection recommendations — 518
If she has not responded to antibiotics and the cultures were not helpful, I recommend
1-Skin biopsy (elipse across edge of lesion) with cultures for fungi and mycobacteria
I would appreciate a follow up.
Sorry for the delay. I was just able to get through to the site.
Evan Farmer 513 — [Cases] Click to review additional cases.
514 — [Main] Click to return to main page.

RuralConsult.com  © 1999 Midwest Center for Rural Health. All rights reserved

METHOD OF FACILITATING MEDICAL CONSULTATIONS

CROSS-REFERENCE TO RELATED APPLICATION

This is a regular utility patent application which claims priority to U.S. provisional patent application Ser. No. 60/243,374, filed Oct. 26, 2000, and assigned to the same assignee as this application. The disclosure of 60/243,374 is hereby incorporated herein by reference.

FIELD OF THE INVENTION

The invention relates to communication methods using computers as communications devices, for example, to facilitate medical consultations, but is believed to be useful in other applications as well.

BACKGROUND OF THE INVENTION

A number of methods for health care providers to consult with each other are known. There are, for example, the methods illustrated and described in U.S. Pat. Nos. 5,307,263; 5,390,238; 5,441,047; 5,779,634; 5,802,494; 5,822,715; 5,855,550; 5,897,493; 5,899,855; 5,911,132; 5,911,687; 5,951,469; 5,989,187; 5,997,476; 6,014,432; 6,022,315; 6,024,699; and, 6,168,563. The disclosures of these references are hereby incorporated herein by reference. No representation is intended by this listing: that this is a complete listing of all pertinent prior art; or that a thorough search of all pertinent prior art has been conducted; or that no better prior art exists; or that the listed references are, or are considered to be, material to patentability. Nor should any of such representations be inferred.

It is not possible for any one health care provider to be proficient in all areas of medicine. A common practice among health care providers is for a first health care provider to consult a second health care provider and have that second health care provider examine the patient and offer a diagnosis and treatment plan. Frequently, when a health care provider needs a consultation, there is no other health care provider immediately available. In a hospital setting, the health care provider can generally call for a consultation from another health care provider with little difficulty. However, in an office setting, the health care provider requiring a consultation must often send the patient to the office of the health care provider he or she wishes to consult. This can work an extreme inconvenience for the patient, who often must travel a great distance to visit the second health care provider.

Therefore, it is desirable to provide a method for health care providers to consult one another regarding diagnosis and treatment of patients. Health care providers in general expend a large portion of their time treating patients, so that often one requiring a consultation is not available to provide a consultation at a time when another one is available to request a consultation. Thus, it is further desirable to provide a method for storing consultation requests until the health care provider being consulted is available. Likewise, it is also desirable to provide a method of storing consultations until the health care provider requesting the consultation is available.

DISCLOSURE OF THE INVENTION

According to an aspect of the invention, a method for a first healthcare provider to consult a second healthcare provider regarding at least one of diagnosis of a patient and treatment of a patient includes the first healthcare provider requesting a consultation on a machine, and the second healthcare provider submitting a consultation response on a machine.

Illustratively according to this aspect of the invention, the first healthcare provider requesting a consultation on a machine and the second healthcare provider submitting a consultation response on a machine together include the first healthcare provider requesting a consultation on a first machine, and the second healthcare provider submitting a consultation response on a second machine coupled to the first machine.

Further illustratively according to this aspect of the invention, the first healthcare provider requesting a consultation on a first machine, and the second healthcare provider submitting a consultation response on a second machine coupled to the first machine together include the first healthcare provider requesting a consultation on a first machine, and the second healthcare provider submitting a consultation response on a second machine coupled to the first machine via a third machine coupled to the first machine and to the second machine.

Additionally illustratively according to this aspect of the invention, the first healthcare provider requesting a consultation on a first machine, and the second healthcare provider submitting a consultation response on a second machine coupled to the first machine via a third machine coupled to the first and second machines includes receiving the request for consultation from the first machine at the third machine, storing the request for consultation on the third machine, sending from the third machine a communication to the second healthcare provider that the request for consultation is awaiting action by the second healthcare provider, the second healthcare provider receiving the communication, and the second healthcare provider gaining access to the third machine to obtain the request for consultation from the third machine.

Illustratively according to this aspect, the invention further includes the second healthcare provider requesting a consultation on the second machine, and a third healthcare provider submitting a consultation response on a fourth machine coupled to the third machine.

Additionally illustratively according to this aspect of the invention, the second healthcare provider requesting a consultation on the second machine, and the third healthcare provider submitting a consultation response on the fourth machine coupled to the second machine via the third machine includes receiving the request for consultation from the second machine at the third machine, storing the request for consultation on the third machine, sending from the third machine a communication to the third healthcare provider that the request for consultation is awaiting action by the third healthcare provider, the third healthcare provider receiving the communication, and the third healthcare provider gaining access to the third machine to obtain the request for consultation from the third machine.

Illustratively according to this aspect, the invention further includes the third machine identifying the request for consultation as pending until one of the second healthcare provider and the third healthcare provider submits a consultation response.

Further illustratively according to this aspect of the invention, one of the second healthcare provider and third healthcare provider submitting a consultation response includes sending a communication from the third machine to the first healthcare provider that the consultation response is awaiting action by the first healthcare provider.

Illustratively according to this aspect, the invention further includes the third machine identifying the request for consultation as fulfilled when the first healthcare provider submits an indication of acceptance of the consultation response.

Additionally illustratively according to this aspect of the invention, requesting a consultation includes submitting at least one of textual queries and textual statements.

Illustratively according to this aspect of the invention, requesting a consultation includes submitting at least one of still images and moving images.

Further illustratively according to this aspect of the invention, requesting a consultation includes submitting sounds.

According to an aspect of the invention, a method permitting one health care provider to consult another health care provider includes permitting the first health care provider to submit a request for a consultation.

Illustratively according to this aspect of the invention, the method includes storing the request until such time that the second health care provider is available to provide the consultation.

Further illustratively according to this aspect of the invention, the method further includes notifying the second health care provider that he or she has a request awaiting action.

Additionally illustratively according to this aspect of the invention, submitting the request includes entering the request on a first client machine capable of generating consultation requests.

Additionally illustratively according to this aspect of the invention, storing the request includes storing the request on a server machine which communicates with the first client machine.

Additionally illustratively according to this aspect of the invention, a request includes at least one of textual queries, textual statements, images, moving images, graphs, and sounds.

Additionally illustratively according to this aspect of the invention, notifying a health care provider that he or she has a consultation request awaiting action includes communicating a notification from the server machine to a second client machine capable of generating consultation responses.

According to another aspect of the invention, a method permitting a second health care provider to submit a response to a request for consultation from a first health care provider includes permitting the second health care provider to submit a consultation response.

Illustratively according to this aspect of the invention, the method further includes storing the response until such time that the first health care provider is available to receive the consultation.

Further illustratively according to this aspect of the invention, the method further includes notifying the first health care provider that he or she has a consultation response awaiting review.

Additionally illustratively according to this aspect of the invention, submitting a response includes entering the response on a client machine capable of generating consultation responses.

Additionally illustratively according to this aspect of the invention, storing a response includes storing the response on a server machine which communicates with the client machine.

Additionally illustratively according to this aspect of the invention, a response includes at least one of textual queries, textual statements, images, moving images, graphs, and sounds.

According to another aspect of the invention, a method of tracking a request for a consultation includes permitting a requesting health care provider to access the request after the request has been submitted for action by a responding health care provider.

Illustratively according to this aspect of the invention, the method further includes storing the request.

Further illustratively according to this aspect of the invention, the method further includes identifying the request as pending, finished, or past.

Additionally illustratively according to this aspect of the invention, a pending request includes a request which has not been responded to by the responding health care provider.

Additionally illustratively according to this aspect of the invention, a finished request includes a request which has been responded to by the responding health care provider, but has not been approved by the requesting health care provider.

Additionally illustratively according to this aspect of the invention, a past request includes a request which has been responded to by the responding health care provider and approved by the requesting health care provider.

BRIEF DESCRIPTION OF THE DRAWINGS

The invention may best be understood by referring to the following detailed description and accompanying drawings which illustrate the invention. In the drawings:

FIGS. 7-8 illustrate a "consult data" page of an illustrative system according to the invention;

FIG. 34 illustrates a Continuing Medical Education (CME) approval page of an illustrative system according to the invention;

DETAILED DESCRIPTIONS OF ILLUSTRATIVE EMBODIMENTS

Figure 1:
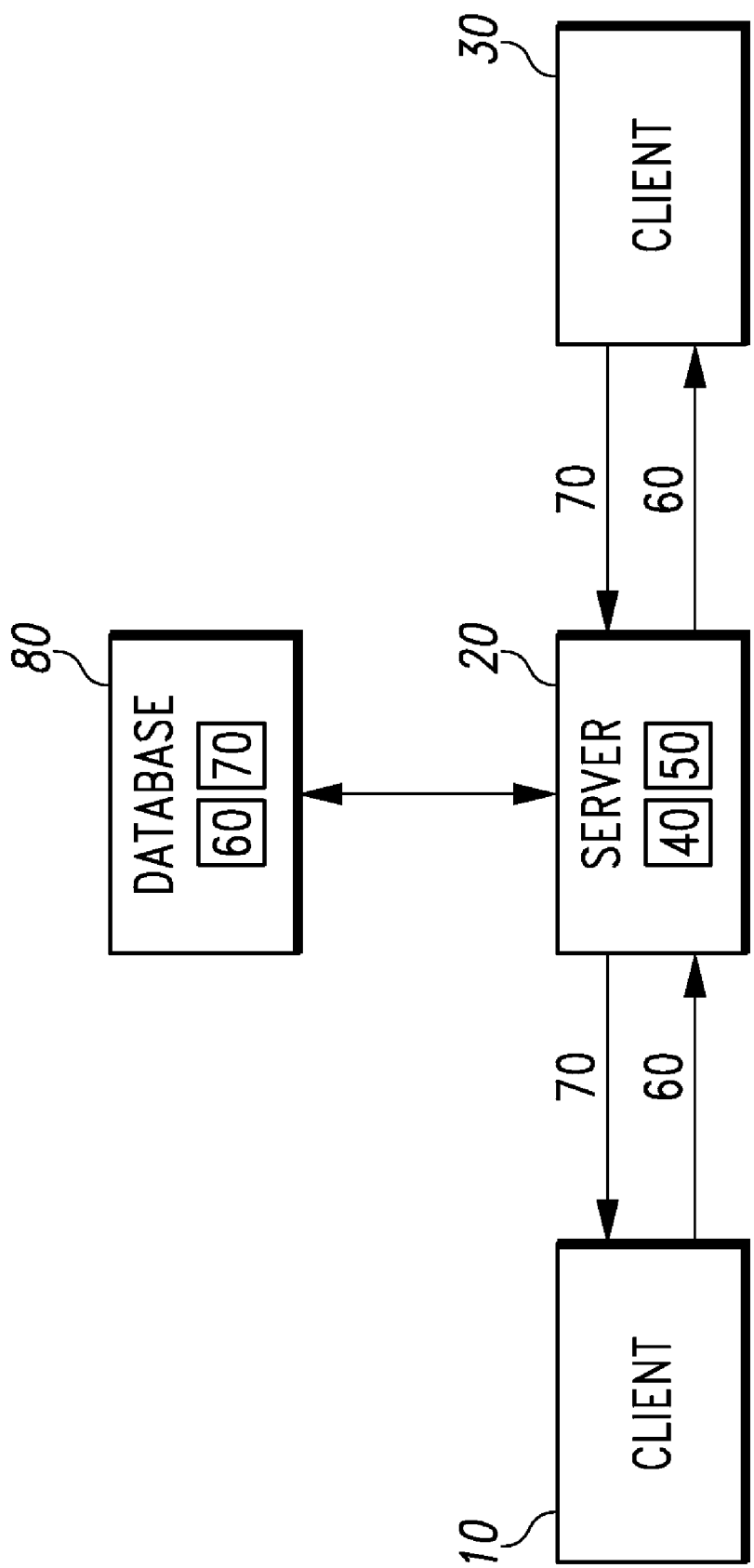
FIG. 1 illustrates a block diagram of apparatus for handling requests for consultation and responses to requests for consultation according to the invention.

Referring now particularly to FIG. 1, health care providers who participate in a consultation arrangement according to the present invention register pertinent information, including their e-mail addresses, with a central location and obtain user names and passwords allowing access to the system. All participating health care providers utilize client machines 10, 30 which communicate with server machine 20 via the internet. Client machines 10, 30 run web client software capable of processing a script language, such as Java.

At least one server machine 20 runs web server software capable of processing a script language, such as Java. The server machine 20 stores a consultation request process 40 and a consultation response process 50 in script form. Furthermore, the server machine 20 stores the requests for a consultation 60 and the responses to requests for a consultation 70 in a database 80.

Figure 2:
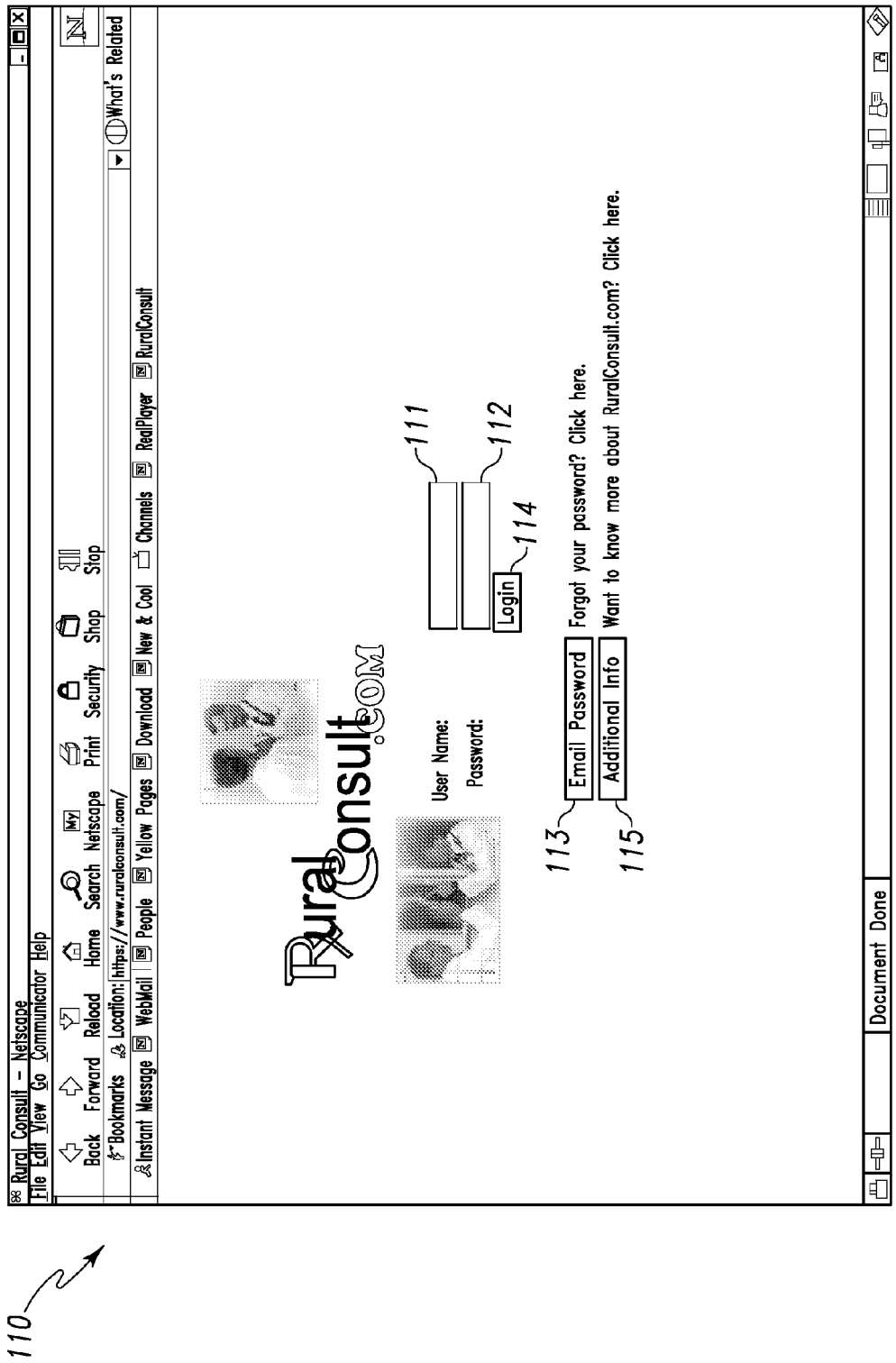
FIG. 2 illustrates a login page of an illustrative system according to the invention.

A first health care provider accesses the system via the client machine 10 by providing the internet address of the server machine 20 to the web client software running on client machine 10. The server machine 20 responds to the client machine 10 with a login page 110, FIG. 2, which is displayed on the client machine 10. The login page 110 contains a "user name" widget 111, a "password" widget 112, an "email password" widget 113, a "login" widget 114 and an "additional info" widget 115.

If the first health care provider cannot remember his or her password, he or she selects the "email password" widget 113, which causes the server machine 20 to e-mail his or her password to his or her registered e-mail address. The first health care provider retrieves the password and returns to home page 110. If the first health care provider desires additional information, he or she selects the "additional info" widget 115, which causes the server machine 20 to display additional information about the system.

Figure 3:
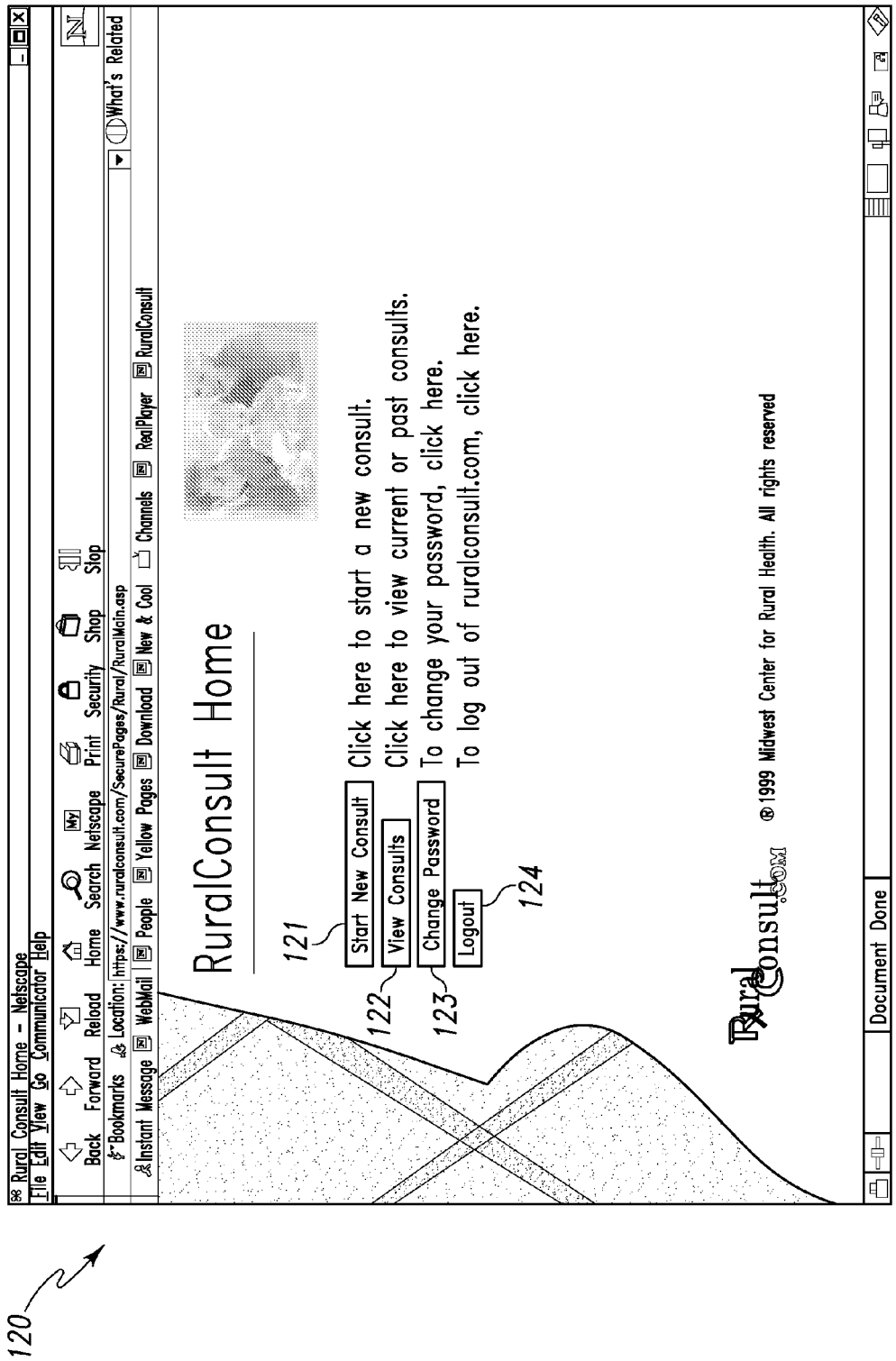
FIG. 3 illustrates a home page of an illustrative system according to the invention.

The first health care provider enters his or her user name into the "user name" widget 111 of the login page 110 and his or her password into the "password" widget 112 of the login page 110. The first health care provider selects the "login" widget 114. The server machine 20 responds with a home page 120. See FIG. 3. The home page 120 includes a "start new consult" widget 121, a "view consults" widget 122, a "change password" widget 123, and a "logout" widget 124.

If the first health care provider selects the "logout" widget 124, the server machine 20 ends his or her session. If the health care provider selects the "change password" widget 123, the server machine 20 responds with a page which permits the health care provider to change his or her password. If health care provider selects the "view consults" widget 122, the server machine 20 responds with a series of pages which permit the health care provider to view past or pending consults.

Figure 4:
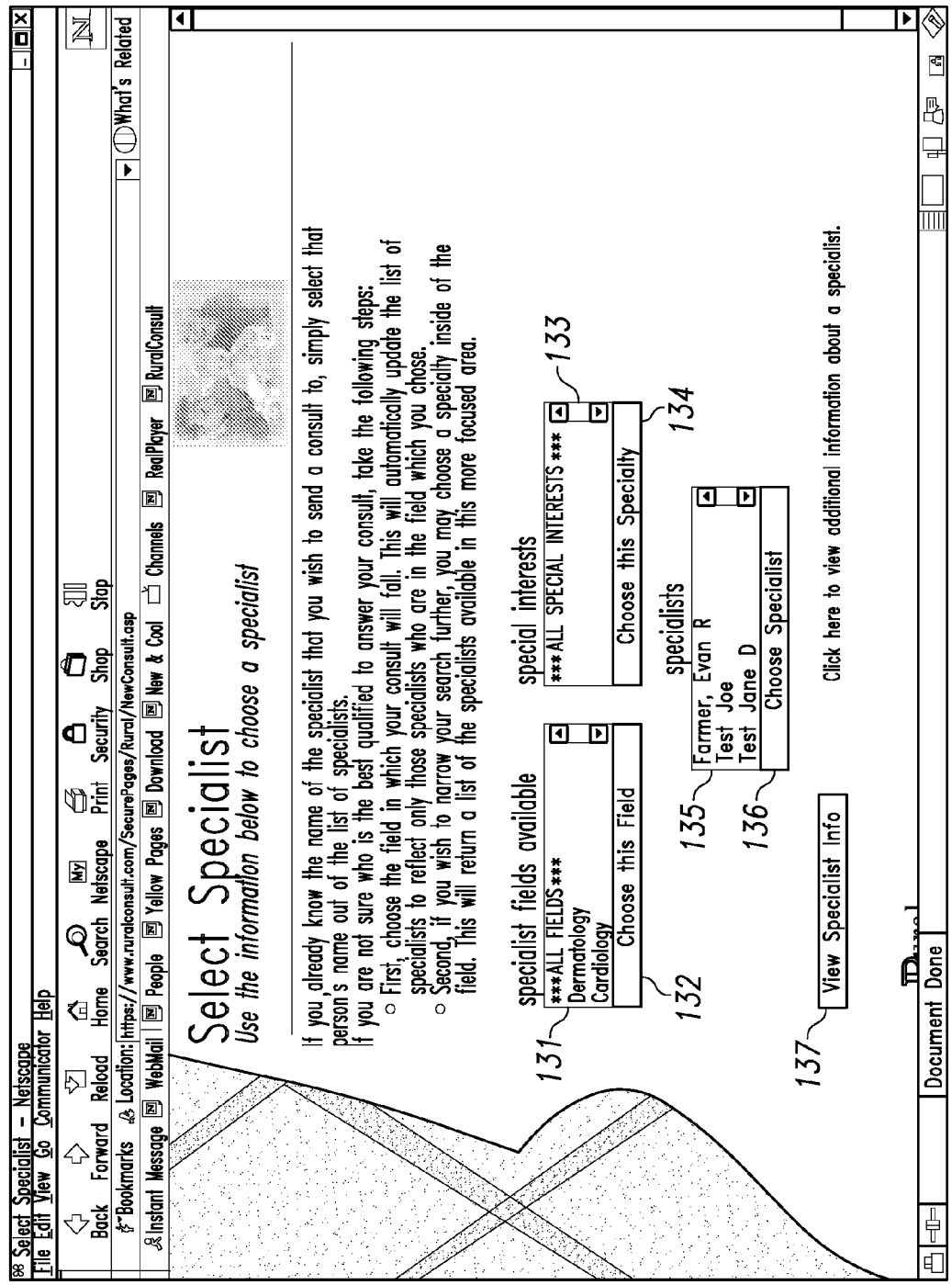
FIG. 4 illustrates a "select specialist" page of an illustrative system according to the invention.
Figure 5:
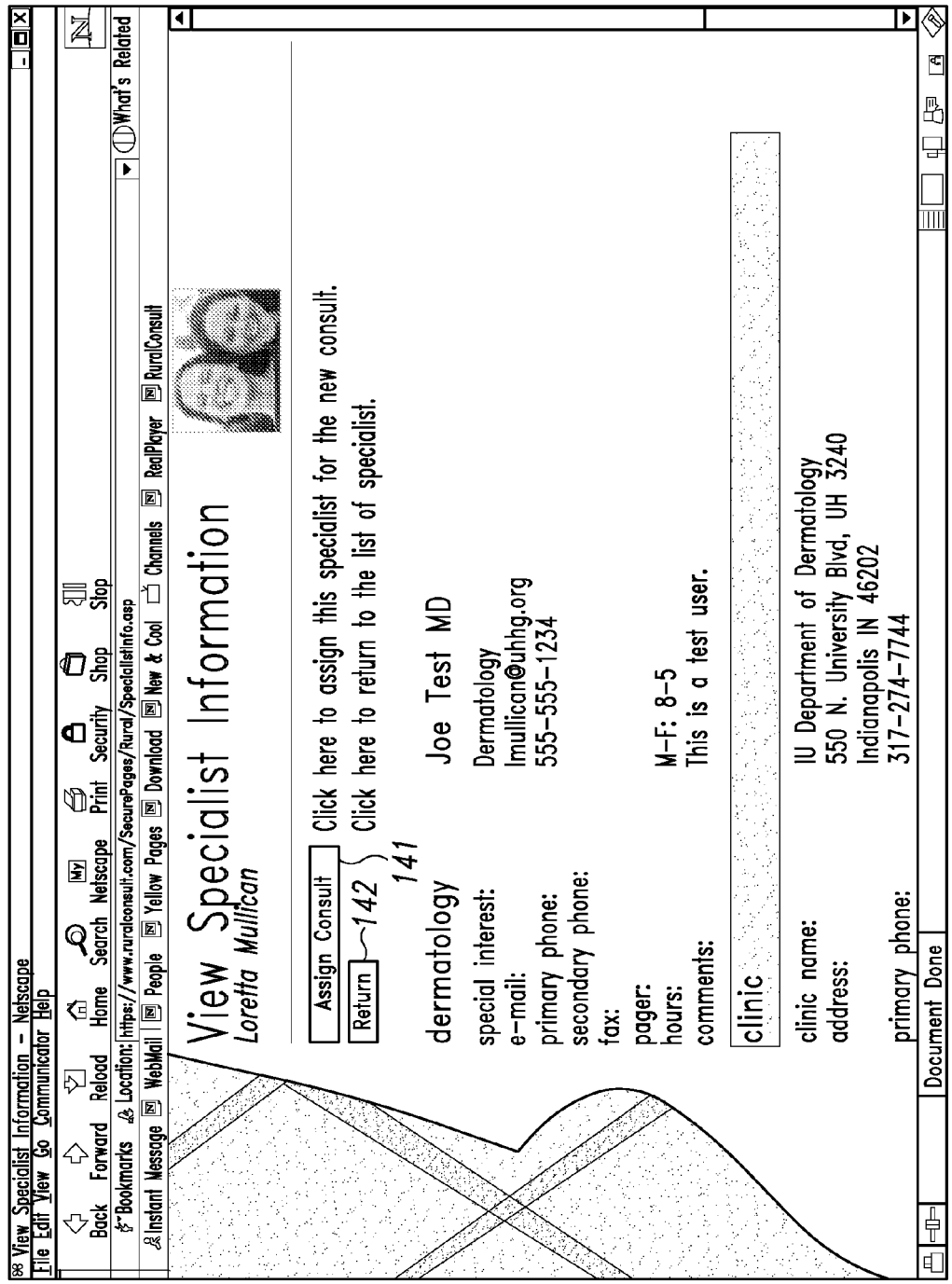
FIG. 5 illustrates a "view specialist information" page of an illustrative system according to the invention.
Figure 6:
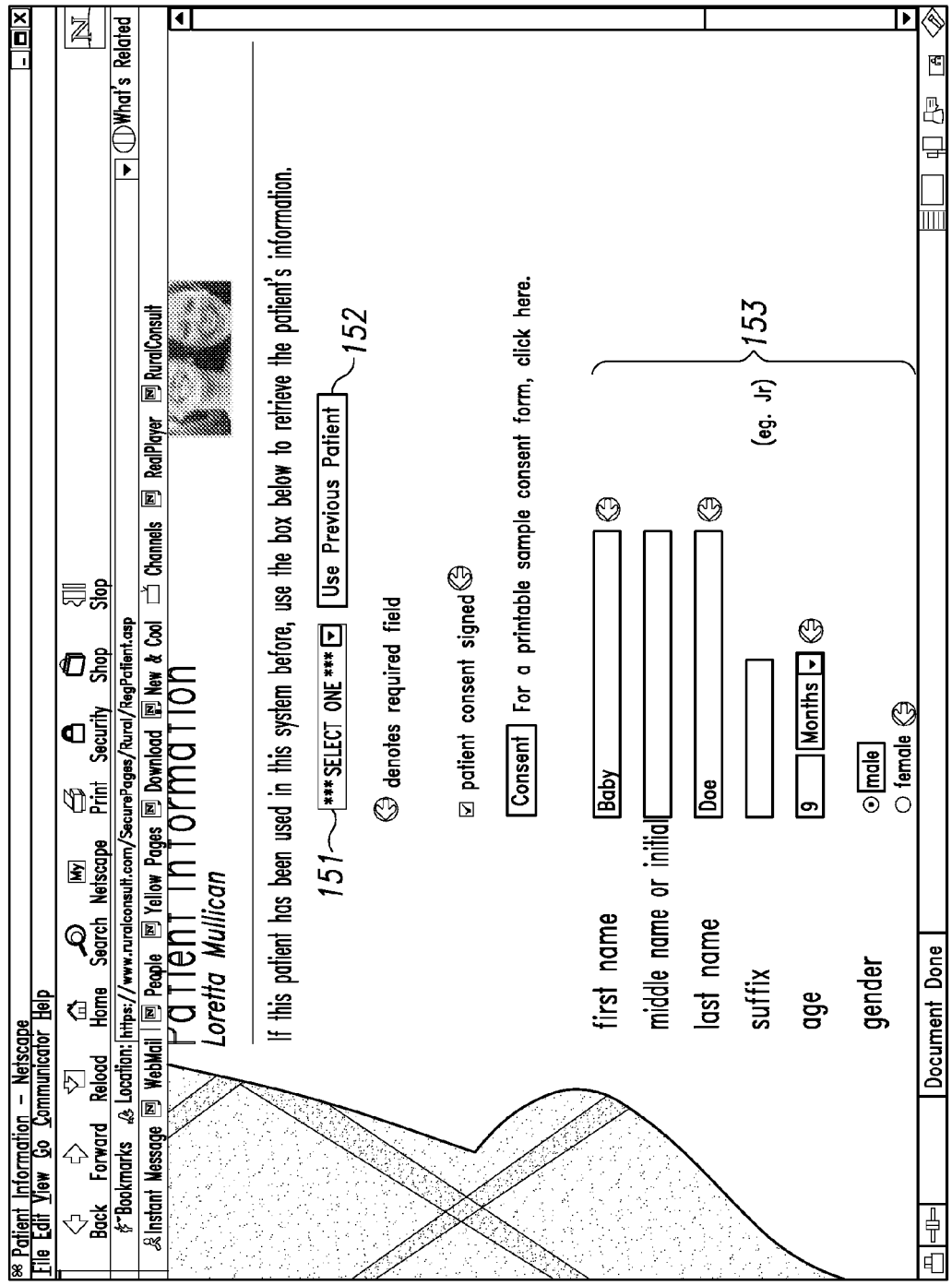
FIG. 6 illustrates a "patient information" page of an illustrative system according to the invention.
Figure 9:
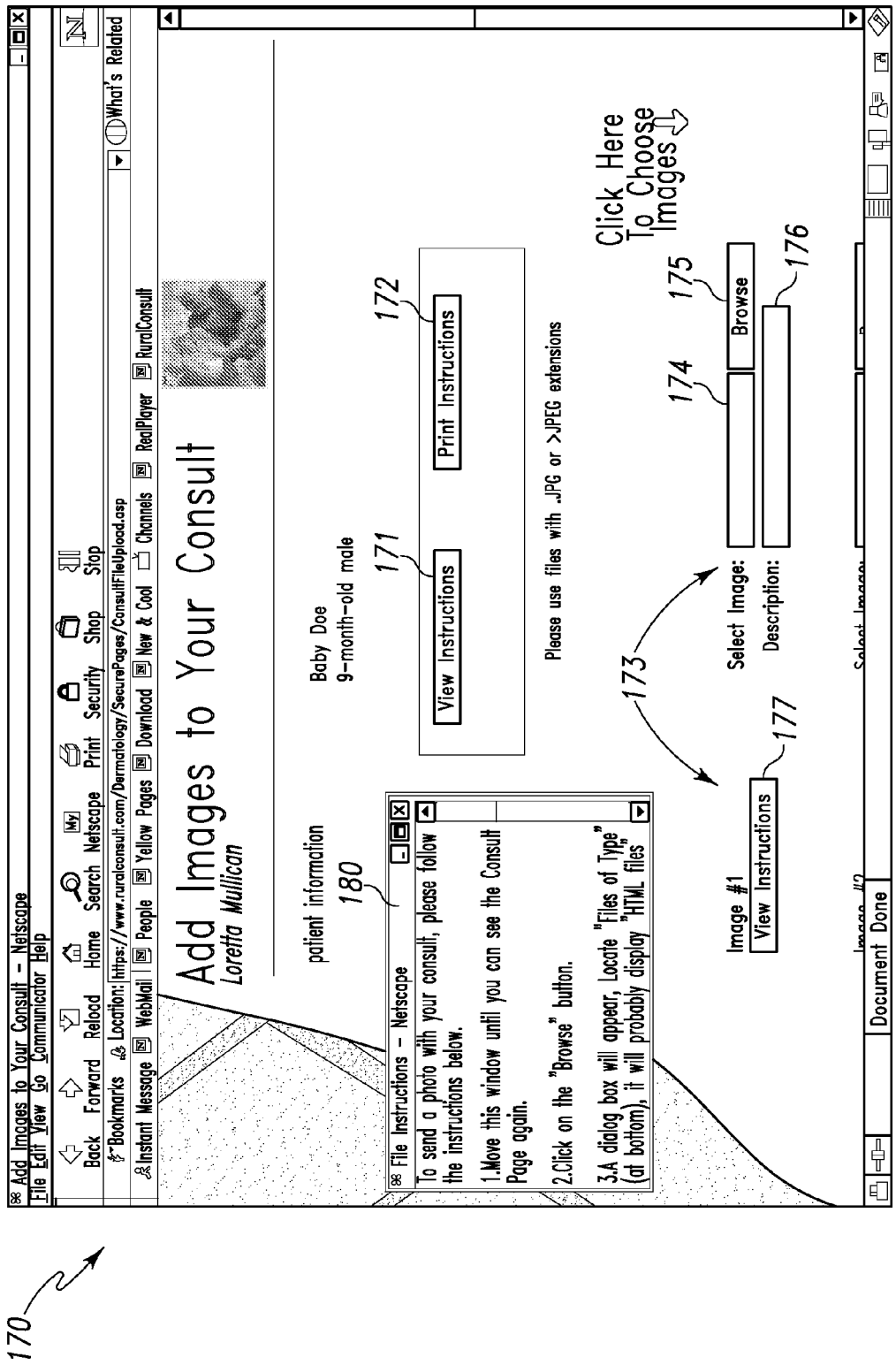
FIGS. 9-13 illustrate an "add images to your consult" page of an illustrative system according to the invention.

If the first health care provider selects the "start new consult" widget 121, server machine 20 responds with a "select specialist" page 130. See FIG. 4. The "select specialist" page 130 includes a "specialist fields available" list widget 131, a "choose this field" widget 132, a "special interests" list widget 133, a "choose this specialty" widget 134, a "specialists" list widget 135, a "choose specialist" widget 136, and a "view specialist info" widget 137. The first health care provider selects a specialist field from the "specialist fields available" widget 131. The health care provider selects the "choose this field" widget 132. The server machine 20 responds by updating the "special interests" list widget 133 and the "specialists" list widget 135. If the health care provider selects a special interest from the "special interests" list widget 133, and selects the "choose this specialty" widget 134, then the server machine 20 responds by further updating the "specialists" list widget 135. The health care provider selects a specialist from the "specialists" list widget 135. If the health care provider selects the "view specialist info" widget 137, the server machine 20 responds with a "view specialist information" page 140. See FIG. 5. The "view specialist information" page 140 includes an "assign consult" widget 141, a "return" widget 142, and specific information regarding the previously selected specialist. If the health care provider selects the "return" widget 142, the server machine 20 responds with the "select specialist" page 130, FIG. 4, which permits the health care provider to select another specialist. If the health care provider selects the "assign consult" widget 141, the server responds with a "patient information" page 150. See FIG. 6. Also, if the health care provider selects the "choose specialist" widget 136 on "select specialist" page 130, FIG. 4, server 20 responds with "patient information" page 150.

"Patient information" page 150 includes a patient selection widget 151, a "use previous patient" widget 152, a group of patient information widgets 153, and a "next" widget 154 (not displayed).

The server machine 20 responds with a "consult data" page 160. See FIGS. 7-8. The "consult data" page 160 includes consult information widgets 161, an "add photos" widget 162, and a "skip photos" widget 163.

Figure 10:
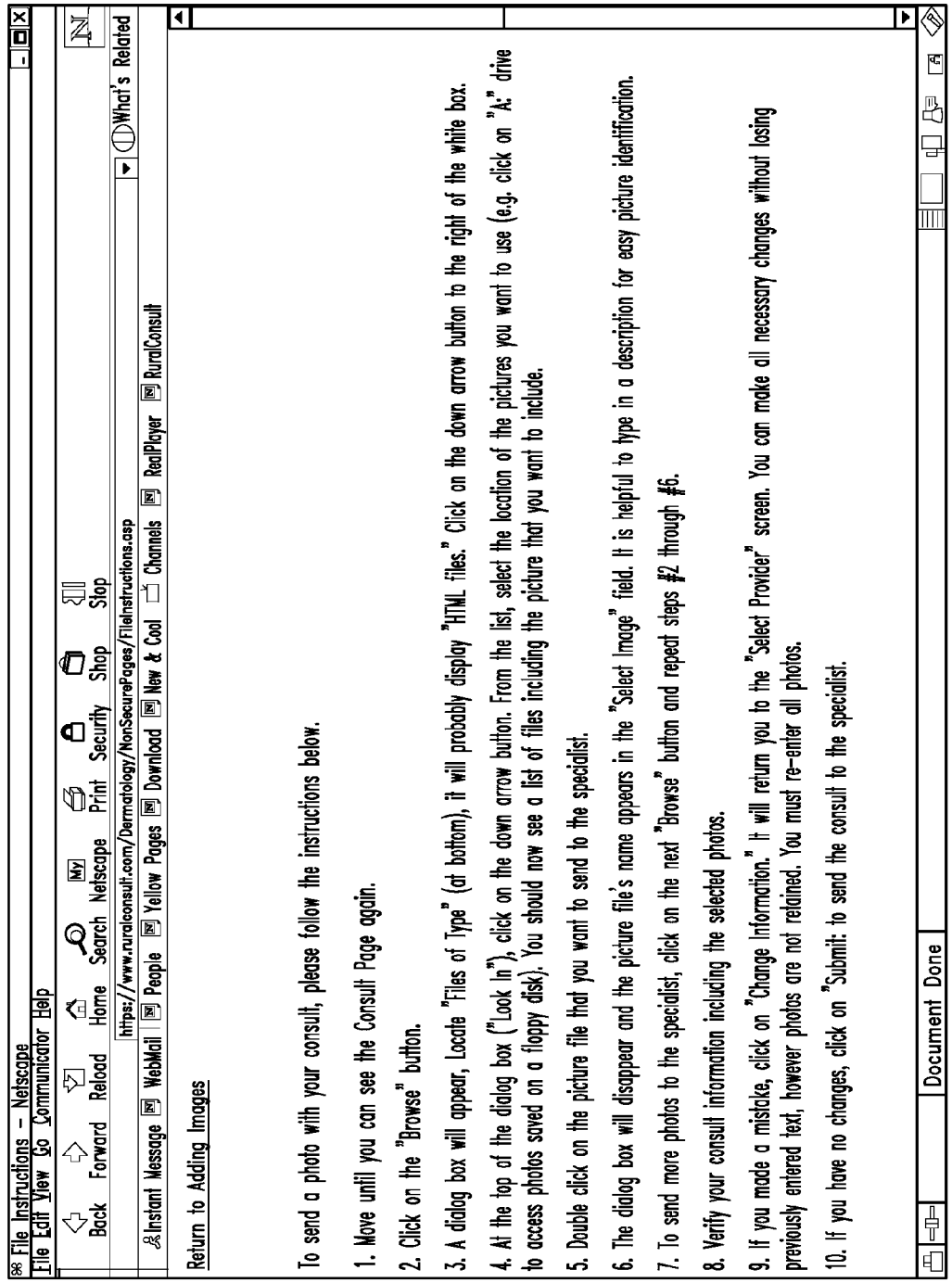
Figure 11:
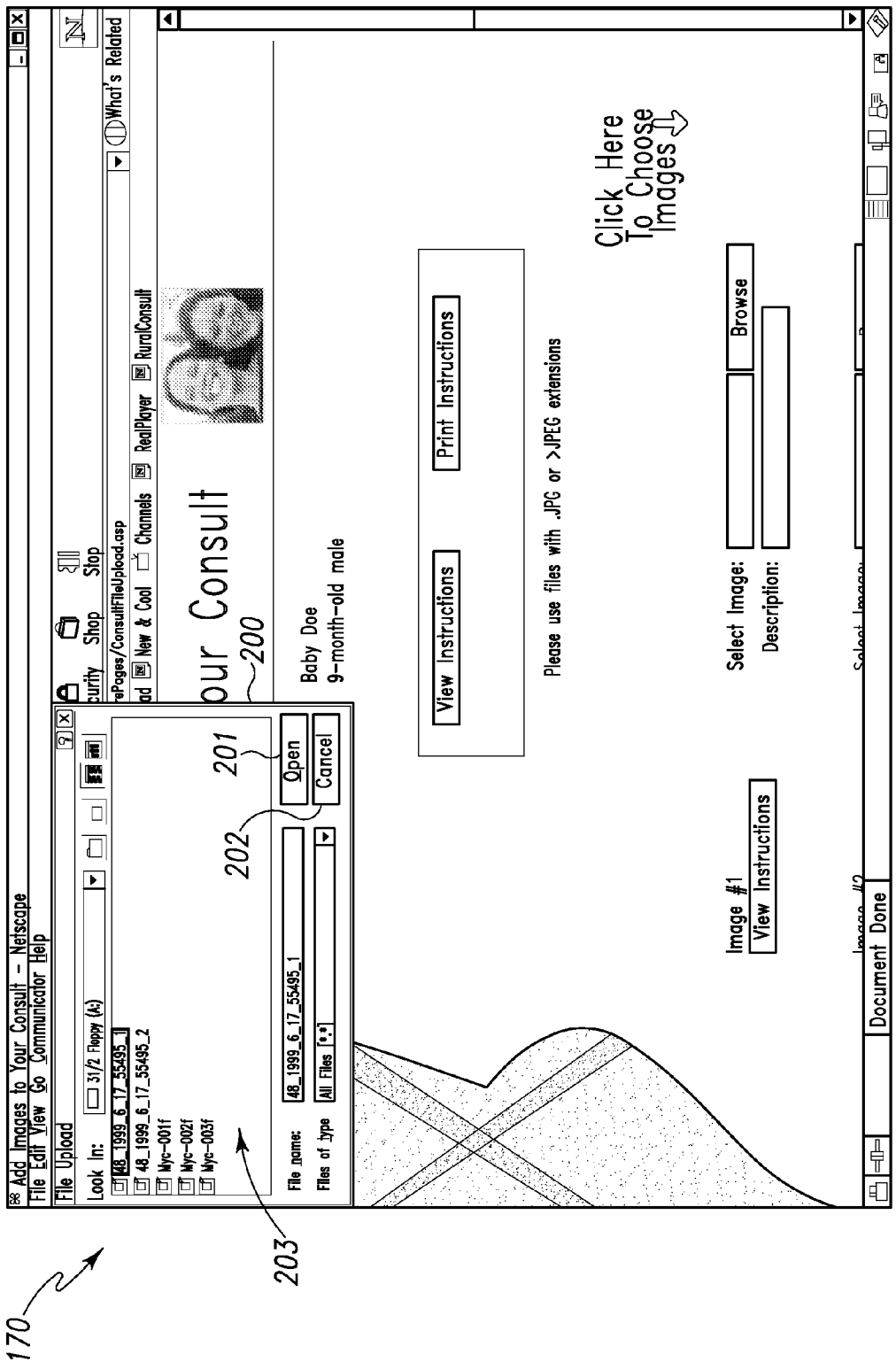
Figure 12:
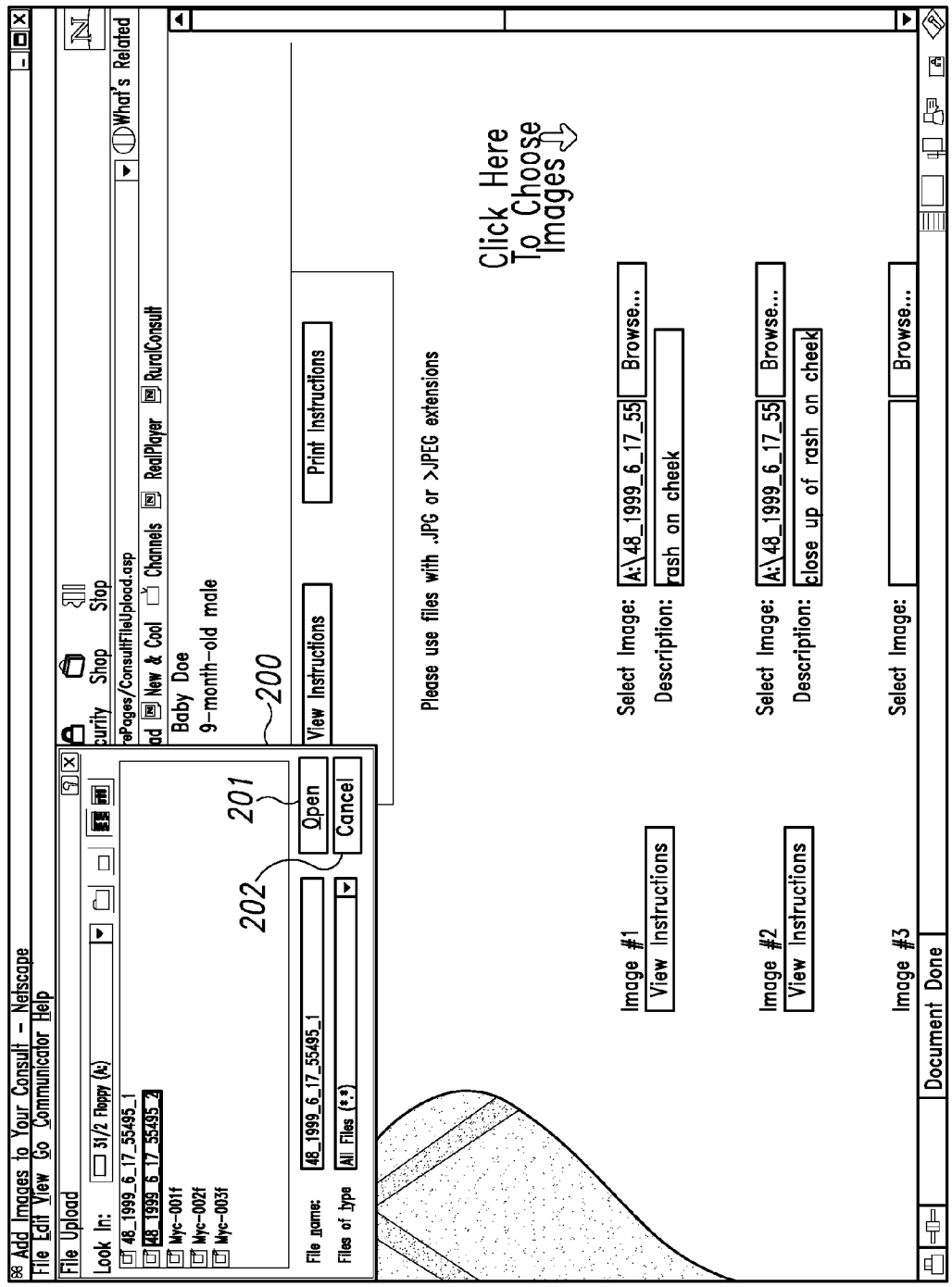
Figure 13:
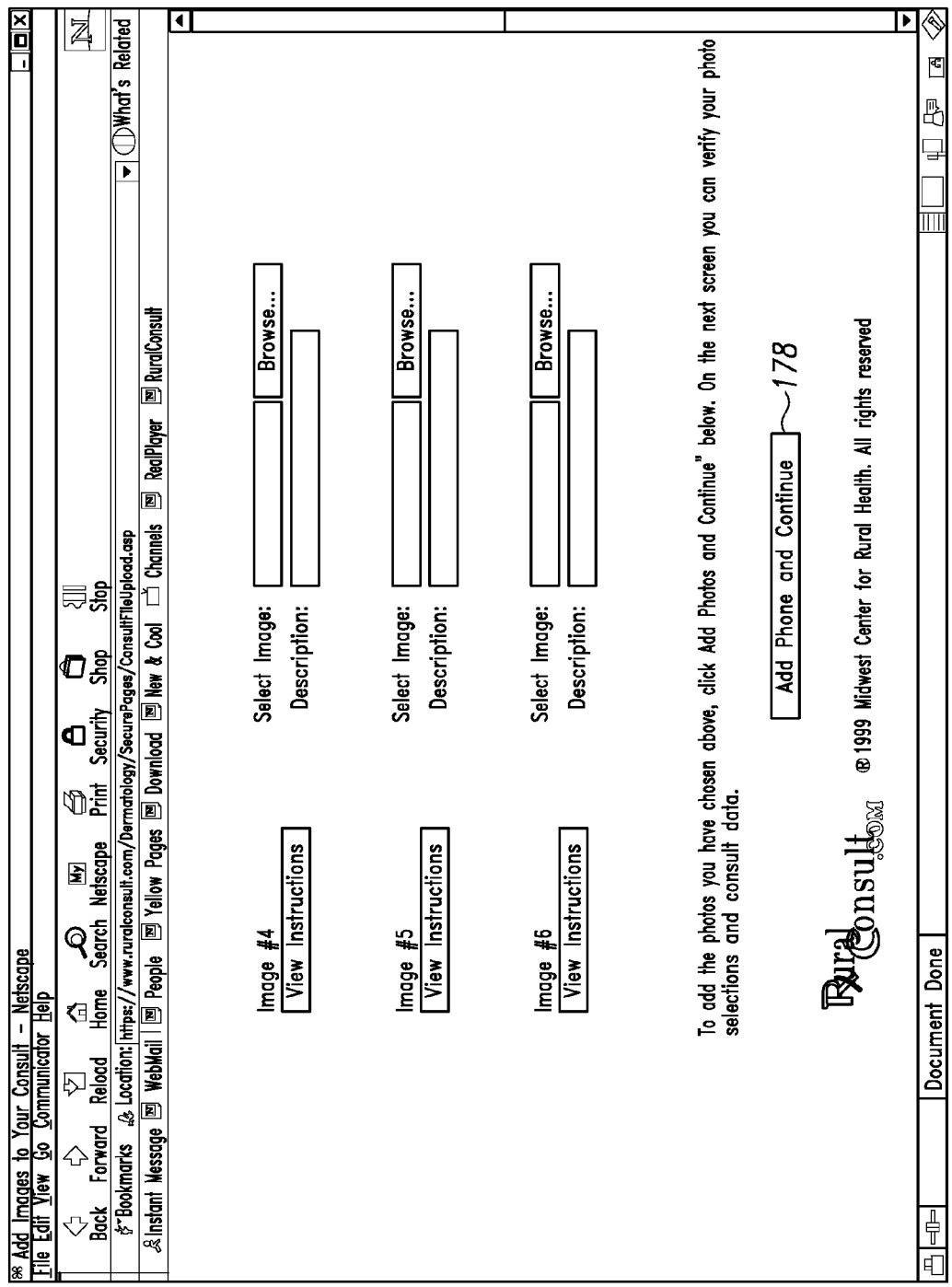
Figure 14:
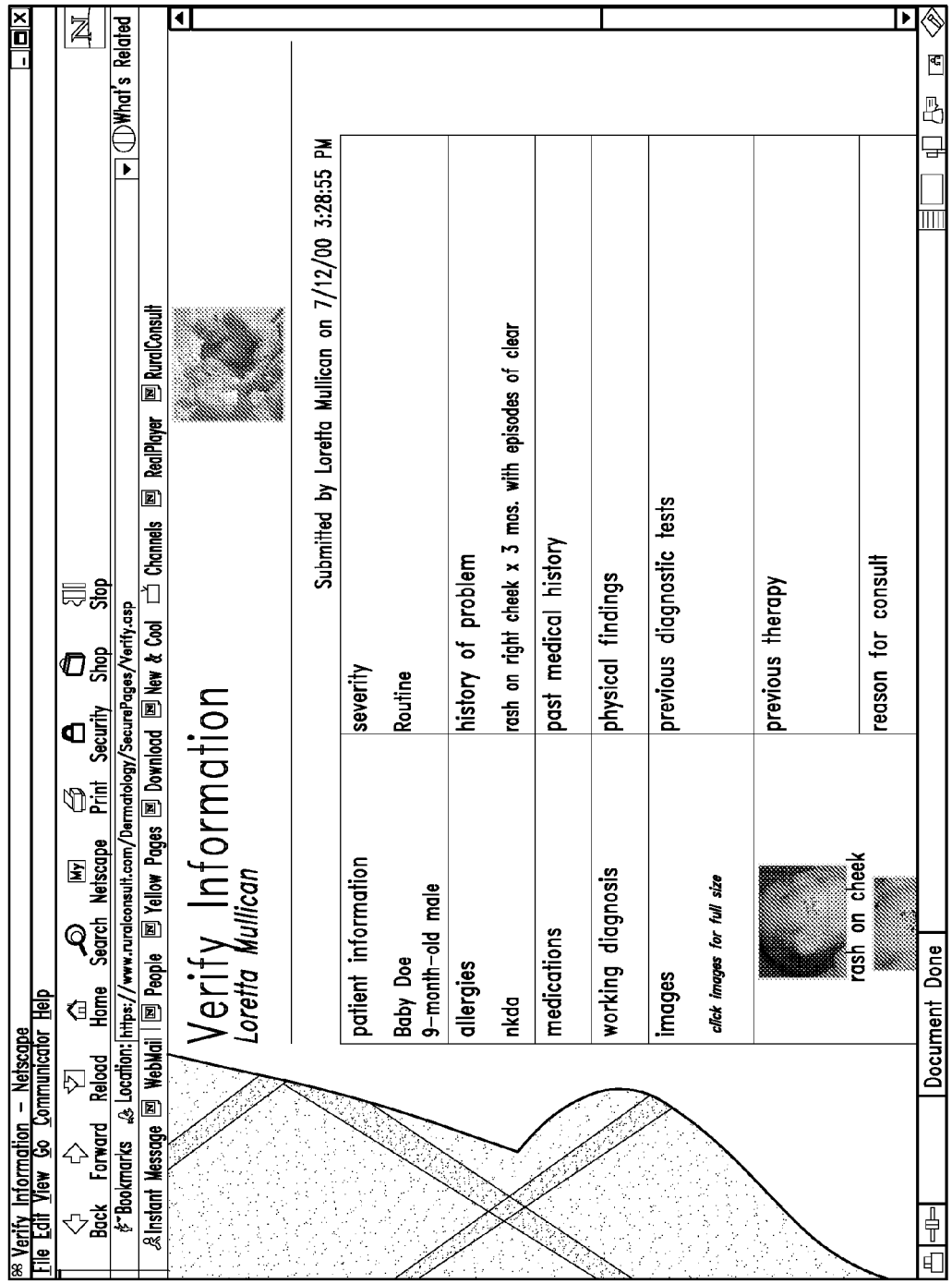
FIGS. 14-18 illustrate a "verify information" page of an illustrative system according to the invention.

If the health care provider selects the "add photos" widget 161, the server machine 20 responds with an "add images to your consult" page 170. See FIGS. 9-13. The "add images to your consult" page 170 includes a "view instructions" widget 171, a "print instructions" widget 172, and six image widget groups 173 for images 1 through 6. Each of the image widget groups 173 contains a "select image" widget 174, a "browse" widget 175, a "description" widget 176, a "view instructions" widget 177, and an "add photos and continue" widget 178, FIG. 13. If the health care provider selects one of the "view instructions" widgets 177, 171, the server machine 20 responds with a pop-up "file instructions" window 180. If the health care provider selects the "print instructions" widget 172, the server machine 20 responds with an instructions page 190, FIG. 10, which is easily printable. The health care provider enters an image file name into "select image" widget 174. Alternatively, the health care provider selects "browse" widget 175, causing the server machine 20 to respond with a "file upload" window 200, FIG. 11. "File upload" window 200 includes an "open" widget 201, a "cancel" widget 202, and a file list widget 203. The health care provider selects a file from the file list widget 203, then selects the "open" widget 201. The server machine 20 responds by automatically entering the name of the selected file in a "select image" widget 174. The health care provider enters a description of the image in the "description" widget 176. When the health care provider has completed this process for up to six images, the health care provider selects the "add photos and continue" widget 178, FIG. 13.

Figure 15:
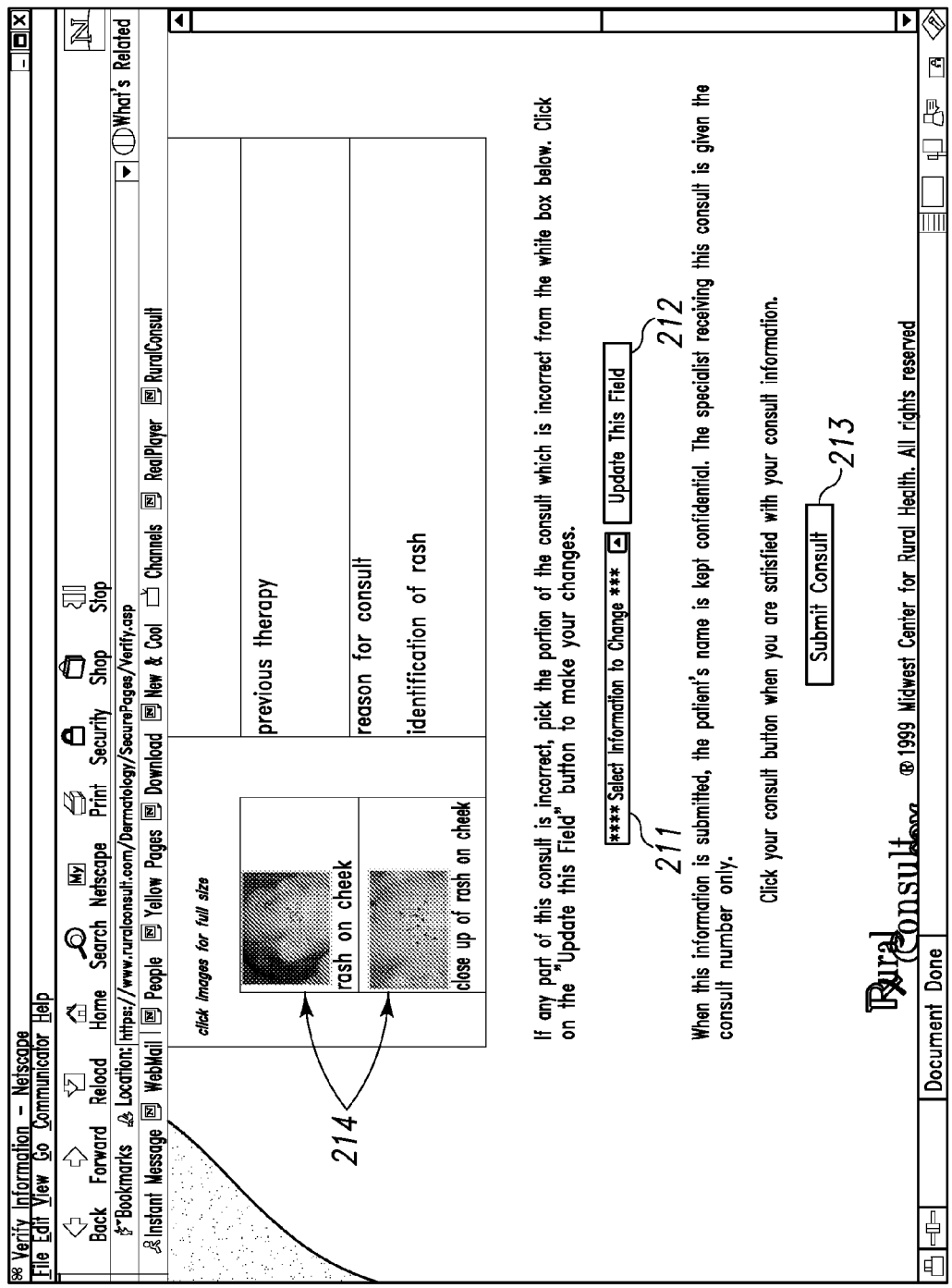
Figure 16:
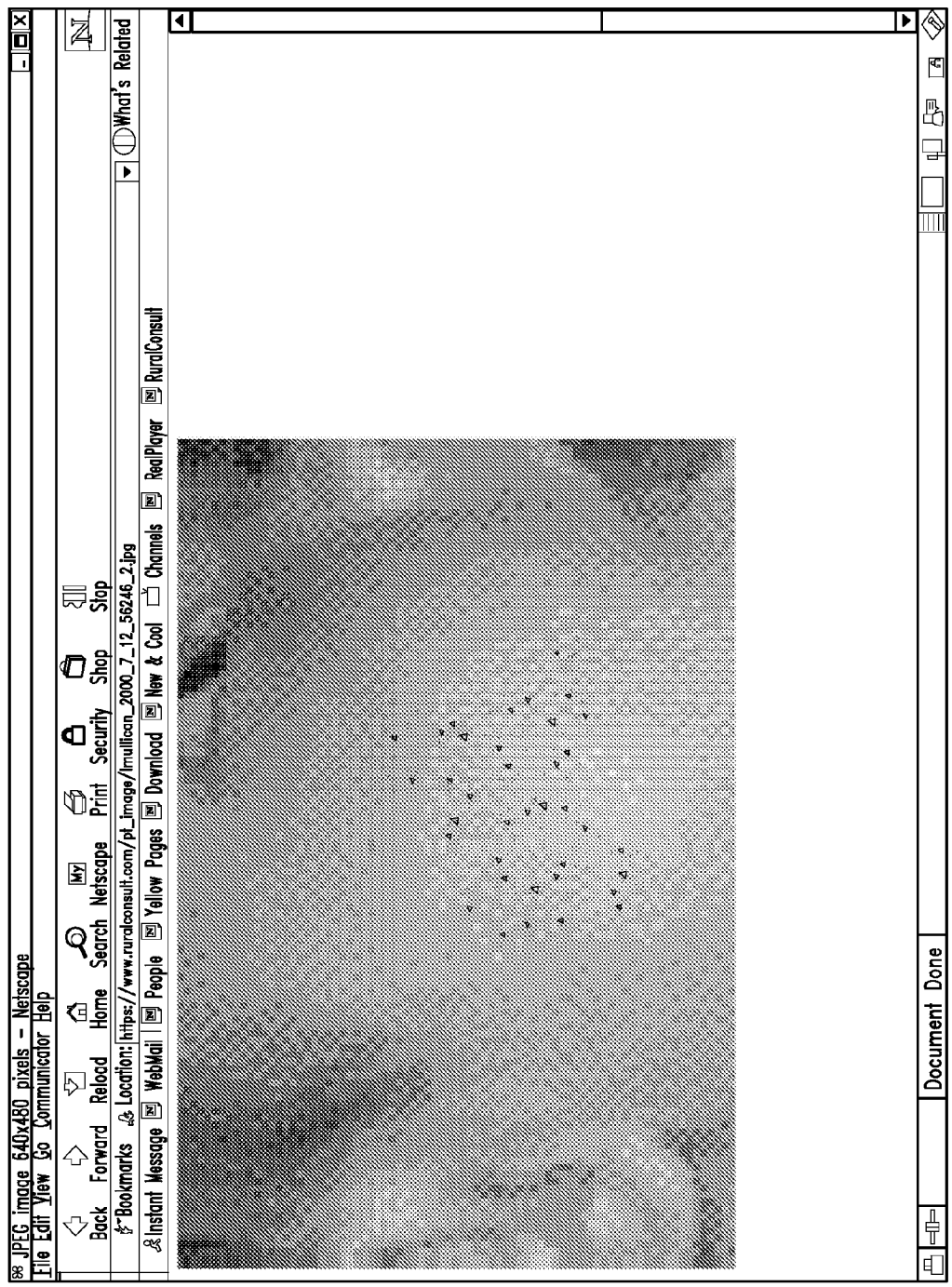
Figure 17:
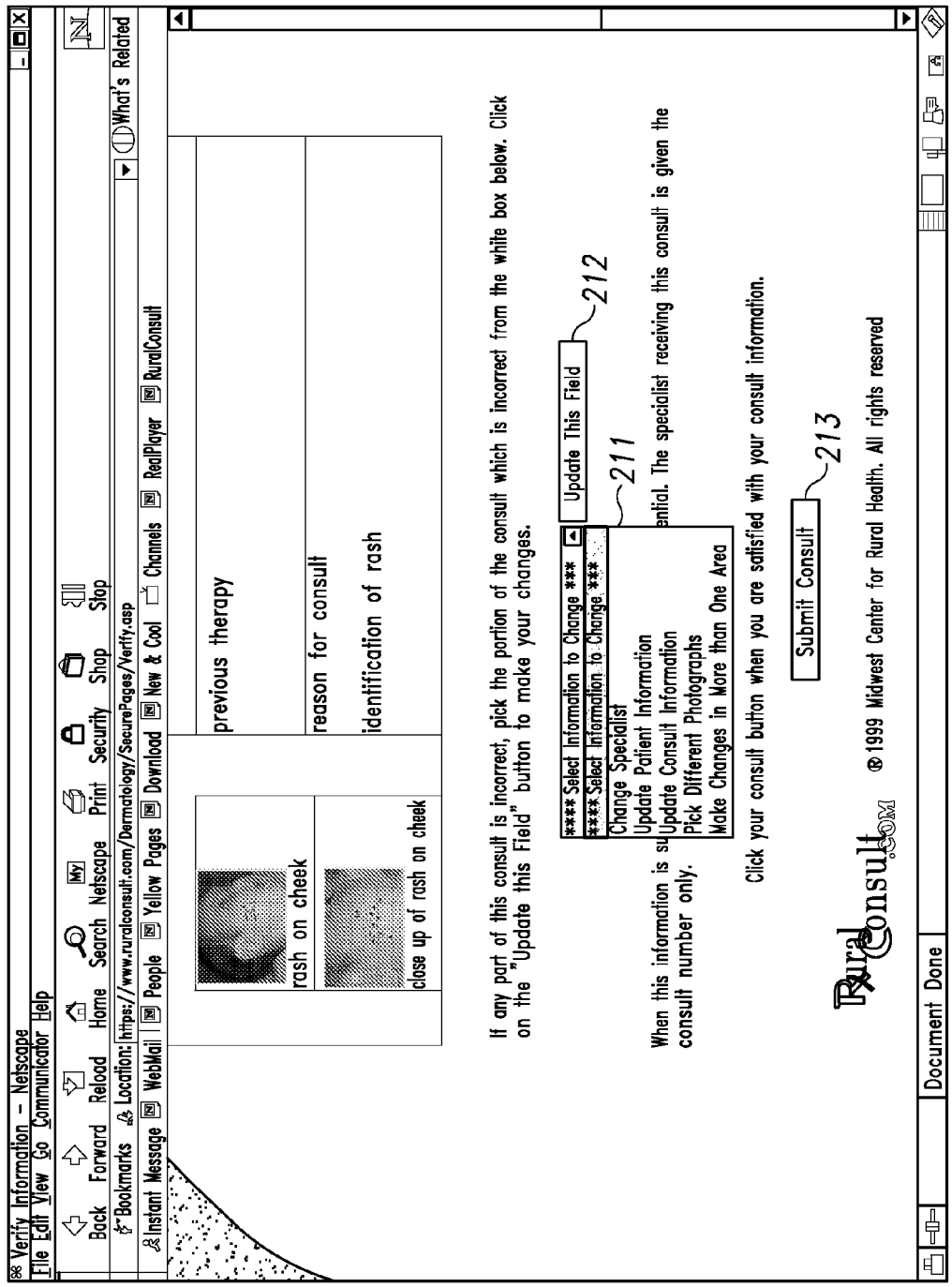
Figure 18:
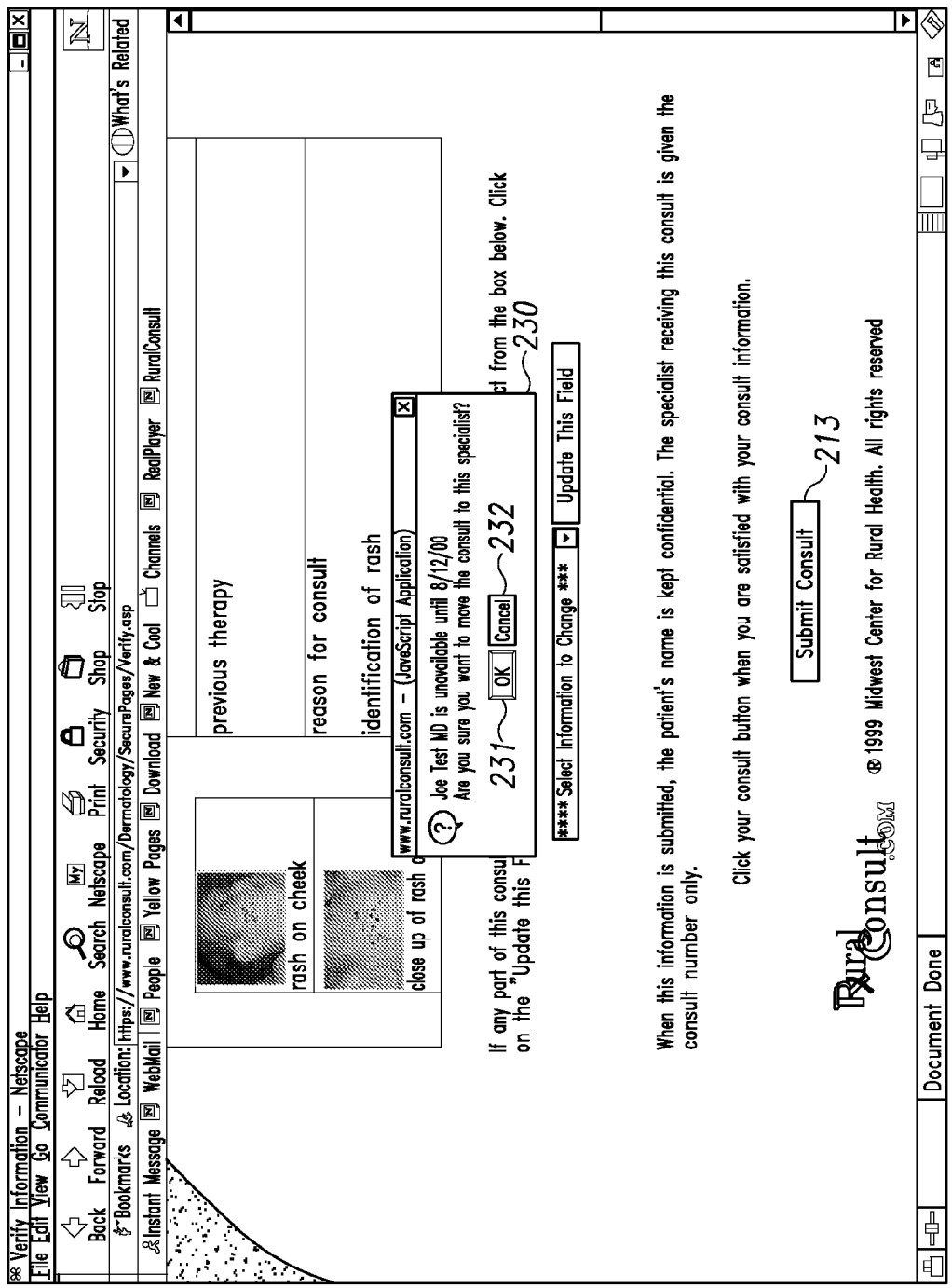

The server responds with a "verify information" page 210. See FIGS. 14-18. "Verify information" page 210 includes a "select information to change" list widget 211, FIG. 15, an "update this field" widget 212, and a "submit consult" widget 213. If the health care provider selects a data item to change from the "select information to change" list widget 211, and selects the "update this field" widget 212, the server responds by returning the health care provider to the page where that data item was originally entered. If the health care provider submitted images, then the "verify information" page 210 includes thumbnail images 214 of those images. If the health care provider selects the thumbnail image 214, the server machine 20 responds with a full size image page 220, FIG. 16. If the selected specialist is unavailable, the server machine 20 responds with a warning window 230, FIG. 18. The warning window 230 includes an "OK" widget 231, and a "cancel" widget 232. If the health care provider selects the "OK" widget 231, then the consult is submitted. If the health care provider selects the "cancel" widget 232, the server machine 20 returns FIG. 15, permitting the health care provider to utilize the "select information to change" widget 211 for the purpose of changing the selected specialist. At last, the health care provider selects the "submit consult" widget 213.

Figure 19:
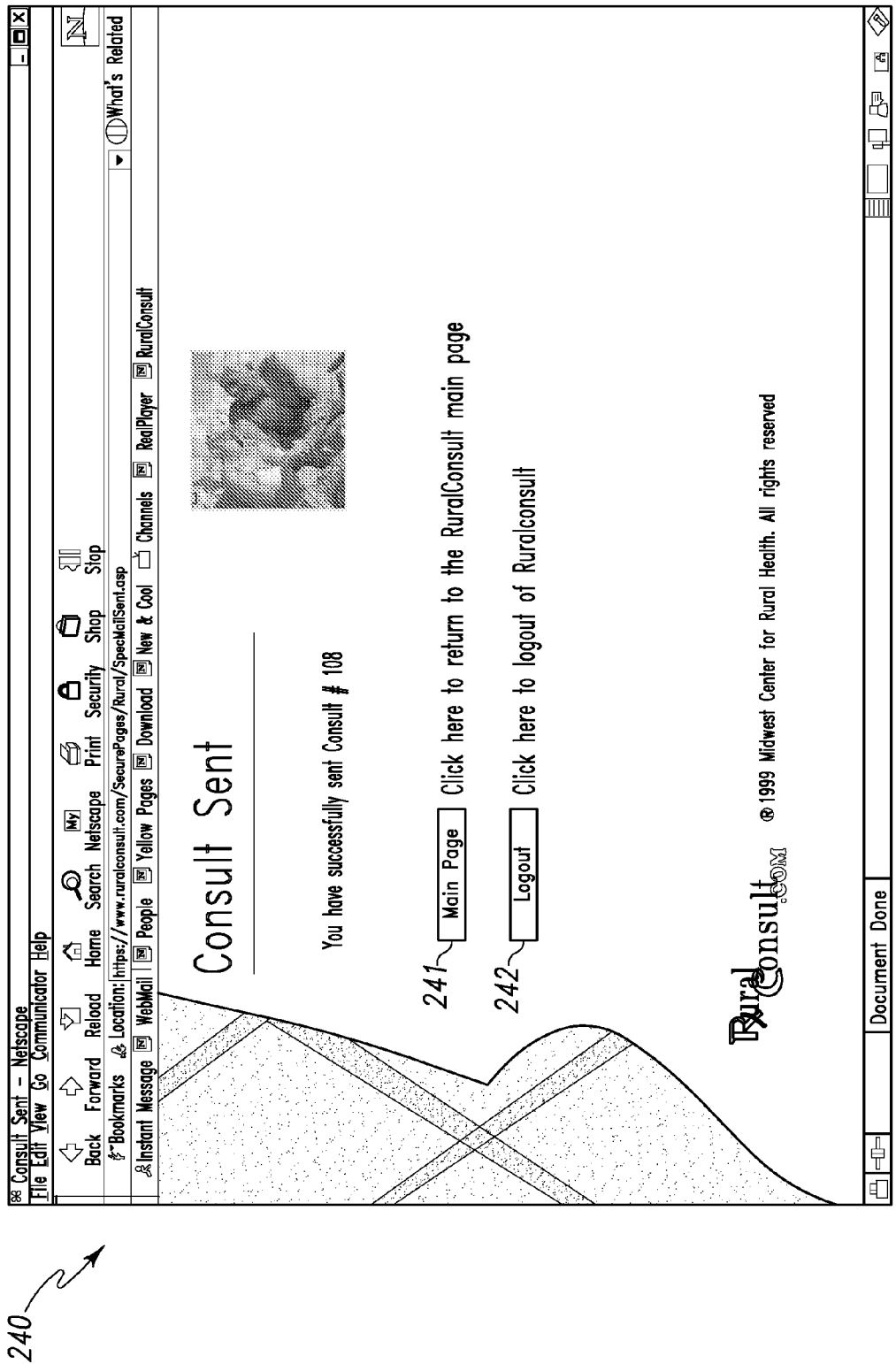
FIG. 19 illustrates a "consult sent" page of an illustrative system according to the invention.

The server machine 20 responds with a "consult sent" page 240. See FIG. 19. The "consult sent" page 240 includes a "main page" widget 241, and a "logout" widget 242. If the health care provider selects the "logout" widget 242, the server machine 20 responds by ending his or her session. If the health care provider selects the "main page" widget 241, he or she is returned to home page 120, FIG. 3.

Figure 20:
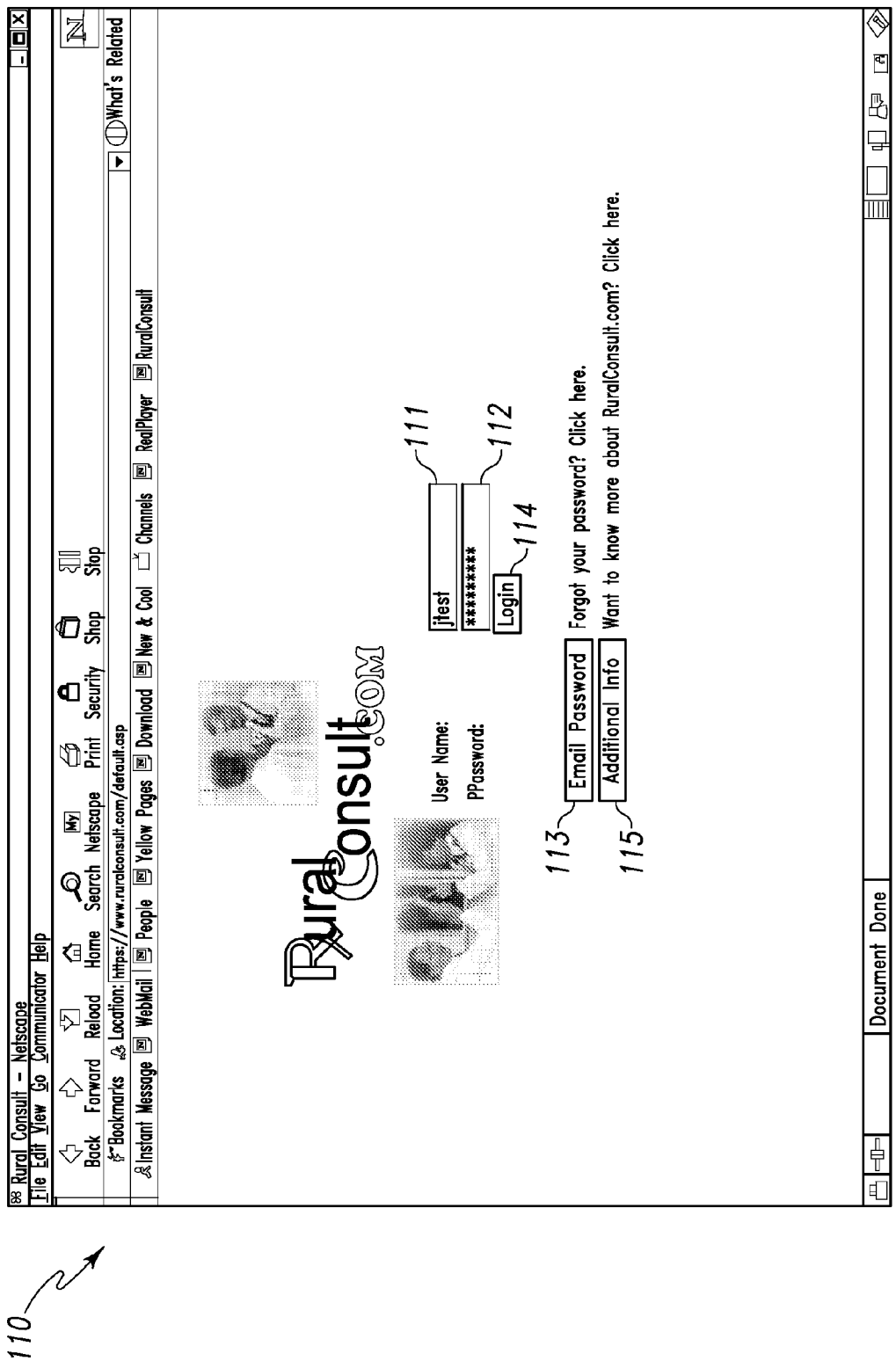
FIG. 20 illustrates a login page of an illustrative system according to the invention.

Once the request for consult is submitted, the server machine 20 sends an e-mail notification to the second health care provider (the specialist selected by the first health care provider) that he or she has a consult waiting. The second health care provider accesses the system via the client machine 30 by providing the internet address of the server machine 20 to the web client software running on the client machine 30. The server machine 20 responds to the client machine 30 with a login page 110. See FIG. 20. The login page 110 contains a "user name" widget 111, a "password" widget 112, an "email password" widget 113, a "login" widget 114, and an "additional info" widget 115.

If the second health care provider desires additional information, he or she selects the "additional info" widget 115, which causes the server machine 20 to display additional information about the system. If the second health care provider cannot remember his or her password, he or she can select the "email password" widget 113, which causes the server machine 20 to email his or her password to his or her registered e-mail address. The second health care provider retrieves the password and returns to home page 110.

Figure 21:
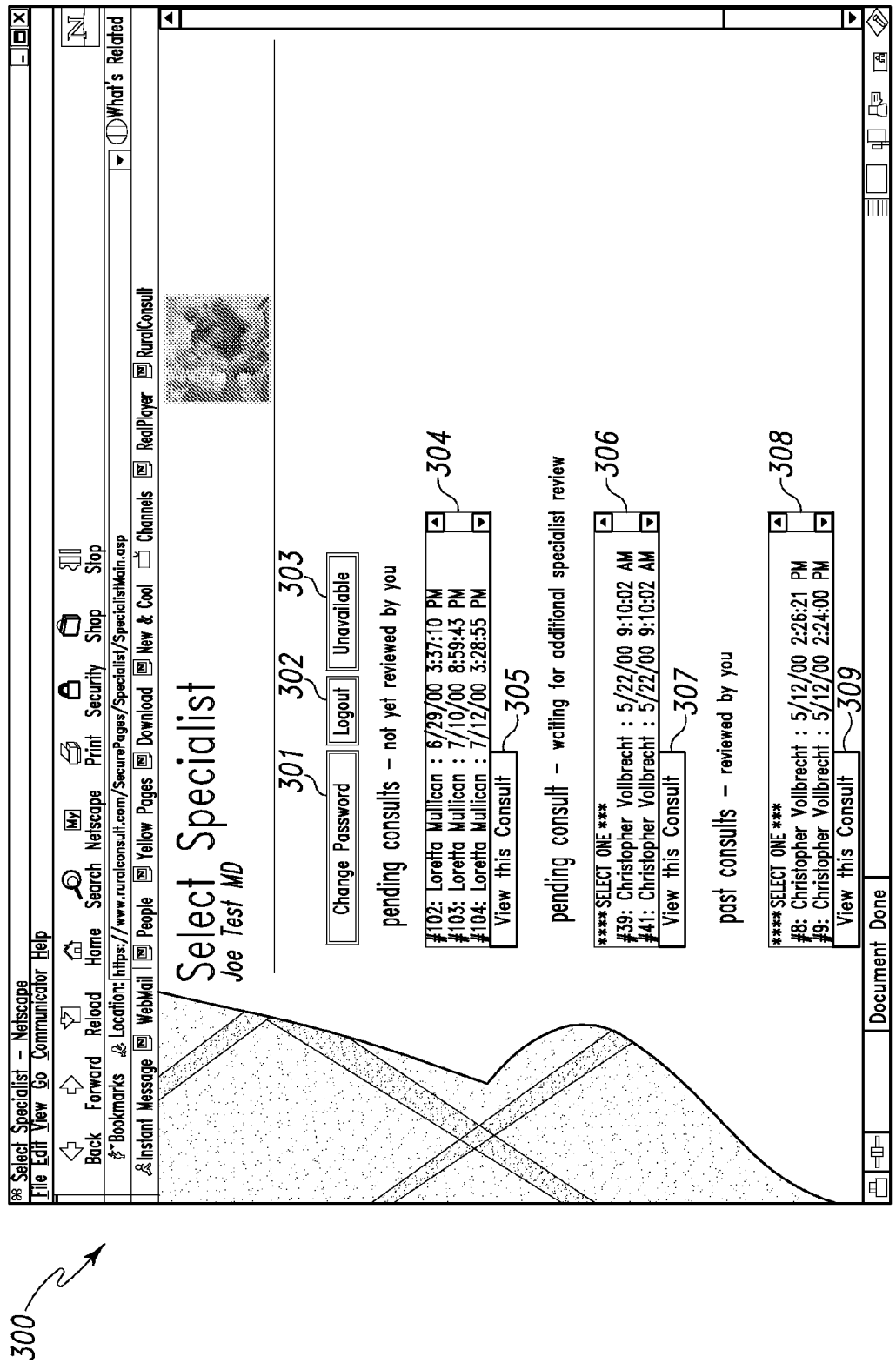
FIG. 21 illustrates a "select consult" page of an illustrative system according to the invention.

The second health care provider enters his or her user name into the "user name" widget 111 and his or her password into the "password" widget 112 of the login page 110. The second health care provider selects the "login" widget 114. The server machine 20 responds with a "select consult" page 300. See FIG. 21.

"Select consult" page 300 includes a "change password" widget 301, a "logout" widget 302, an "unavailable" widget 303, a first "pending consults" widget list 304, a first "view this consult" widget 305, a second "pending consult" widget 306, a second "view this consult" widget 307, a "past consults" widget list 308, and a third "view this consult" widget 309. The second health care provider selects a consult from consult list widget 304, 306, or 308, and then selects the corresponding "view this consult" widget 305, 307, or 309.

Figure 22:
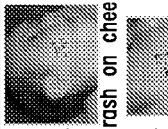
FIGS. 22-24 illustrate a "consult data" page of an illustrative system according to the invention.

The server machine 20 responds with a "consult data" page 310. See FIGS. 22-24. The "consult data" page 310 includes consult data form 311, a "forward" widget 313, FIG. 23, an "assessment/diagnosis" widget 314, a "differential diagnosis" widget 315, a "recommendations" widget 316, a "submit my comments" widget 317 and a "main page" widget 318. The consult data form 311 includes several data fields and thumbnail images 312, FIGS. 22-23. If the health care provider selects a thumbnail image 312, the server machine 20 responds with a full size image page 320, FIG. 24. The health care provider enters his or her assessment and diagnosis into "assessment/diagnosis" widget 314, enters his or her differential diagnosis into "differential diagnosis" widget 315, enters his or her recommendations into "recommendations" widget 316, and selects "submit my comments" widget 317.

Figure 25:
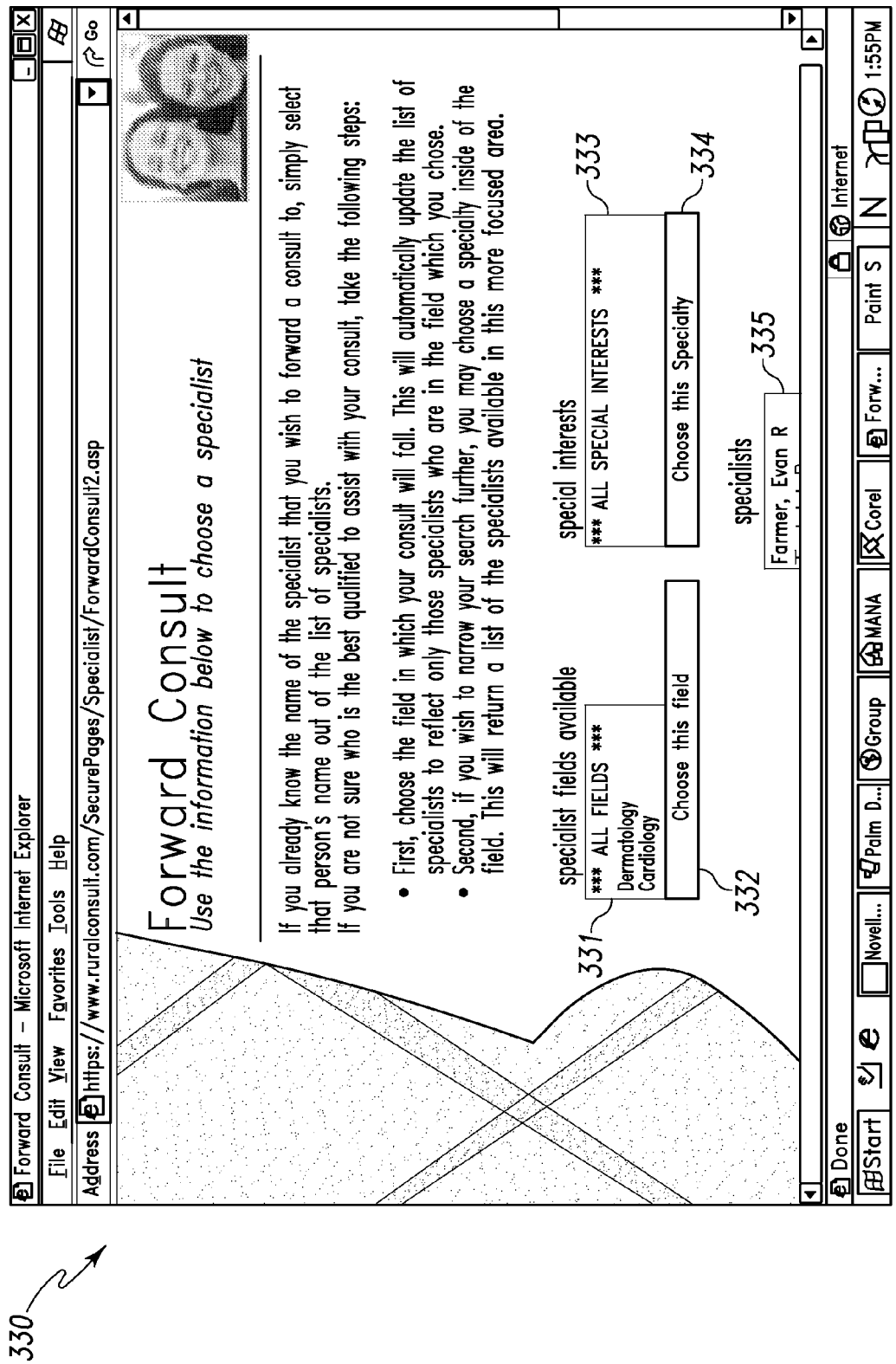
FIGS. 25-26 illustrate a "forward consult" page of an illustrative system according to the invention.
Figure 26:
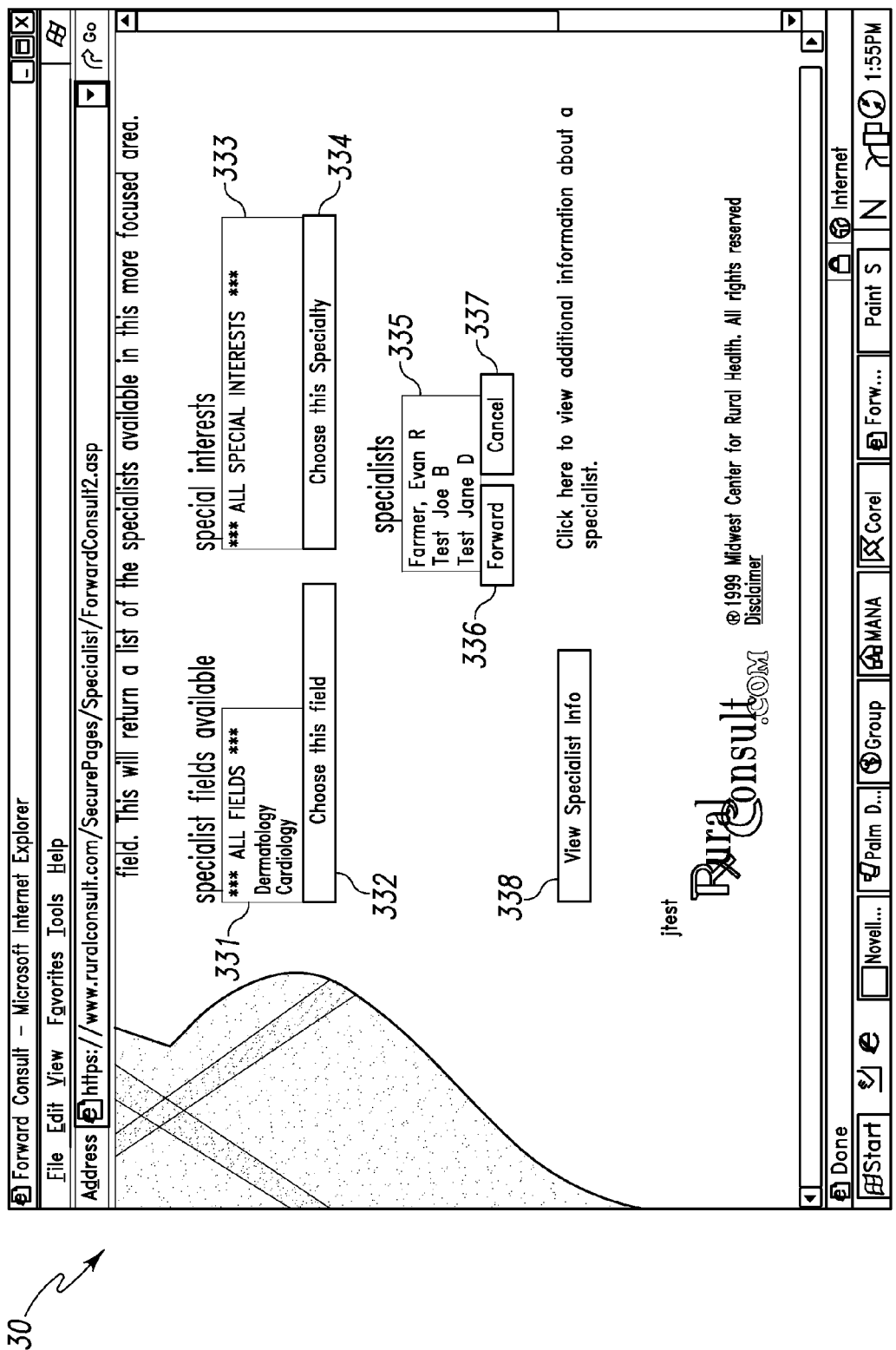

Alternatively, the health care provider may select "forward" widget 313, in order to forward the consult data to another specialist. If the health care provider selects "forward" widget 313, the server machine 20 responds with a "forward consult" page 330. See FIGS. 25-26. If the health care provider selects the "submit my comments" widget 317, the server machine 20 responds with a "thank you" page 340. See FIG. 27. If the health care provider selects "main page" widget 318, FIG. 23, server machine 20 responds with select consult page 300, FIG. 21.

The "forward consult" page 330 includes a "specialist fields available" widget 331, a "choose this field" widget 332, a "special interests" list widget 333, a "choose this specialty" widget 334, a "specialists" list widget 335, a "forward" widget 336, a "cancel" widget 337, and a "view specialist info" widget 338. The second health care provider selects a specialist field from the "specialist fields available" widget 331. The health care provider selects the "choose this field" widget 332. The server machine 20 responds by updating the "special interests" list widget 333 and the "specialists" list widget 335. If the second health care provider selects a special interest from the "special interests" list widget 333, and selects the "choose this specialty" widget 334, then the server machine 20 responds by further updating the "specialists" list widget 335. The health care provider selects a specialist from the "specialists" list widget 335. If the health care provider selects the "view specialist info" widget 338, the server machine 20 responds by briefly displaying information about the selected specialist. The health care provider may select the "forward" widget 336. Alternatively, the health care provider may select the "cancel" widget 337, which causes the server to cancel the forward operation and respond with consult data page 310, FIGS. 22-24.

Figure 28:
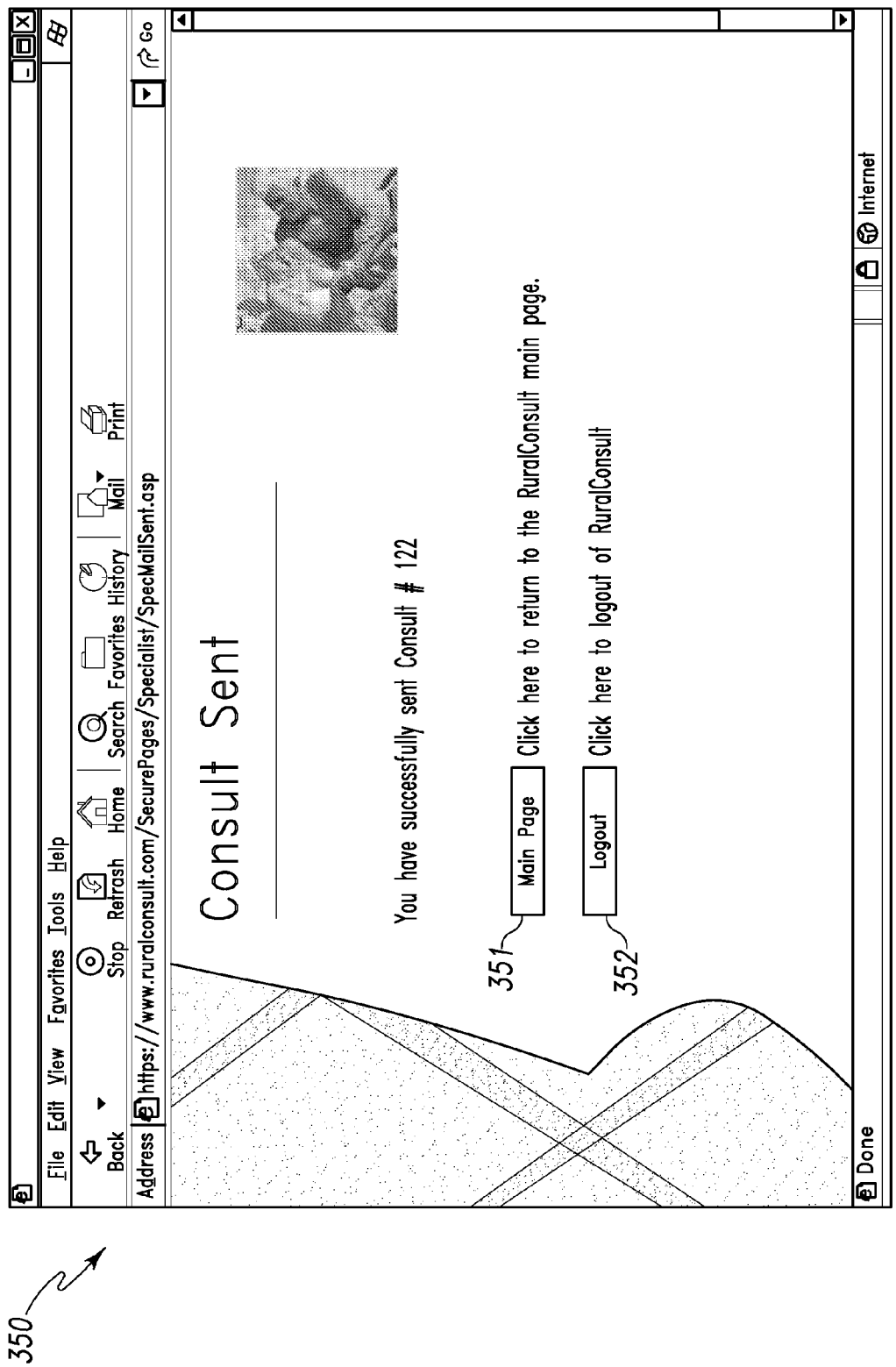
FIG. 28 illustrates a "consult sent" page of an illustrative system according to the invention.

The server machine 20 responds to the selection of the "forward" widget 336 with a "consult sent" page 350, FIG. 28. "Consult sent" page 350 includes a "main page" widget 351 and a "logout" widget 352. If the health care provider selects "logout" widget 352, the server machine 20 responds with login page 110, FIG. 20. If the health care provider selects "main page" widget 351, server machine 20 responds with "select consult" page 300, FIG. 21.

Figure 27:
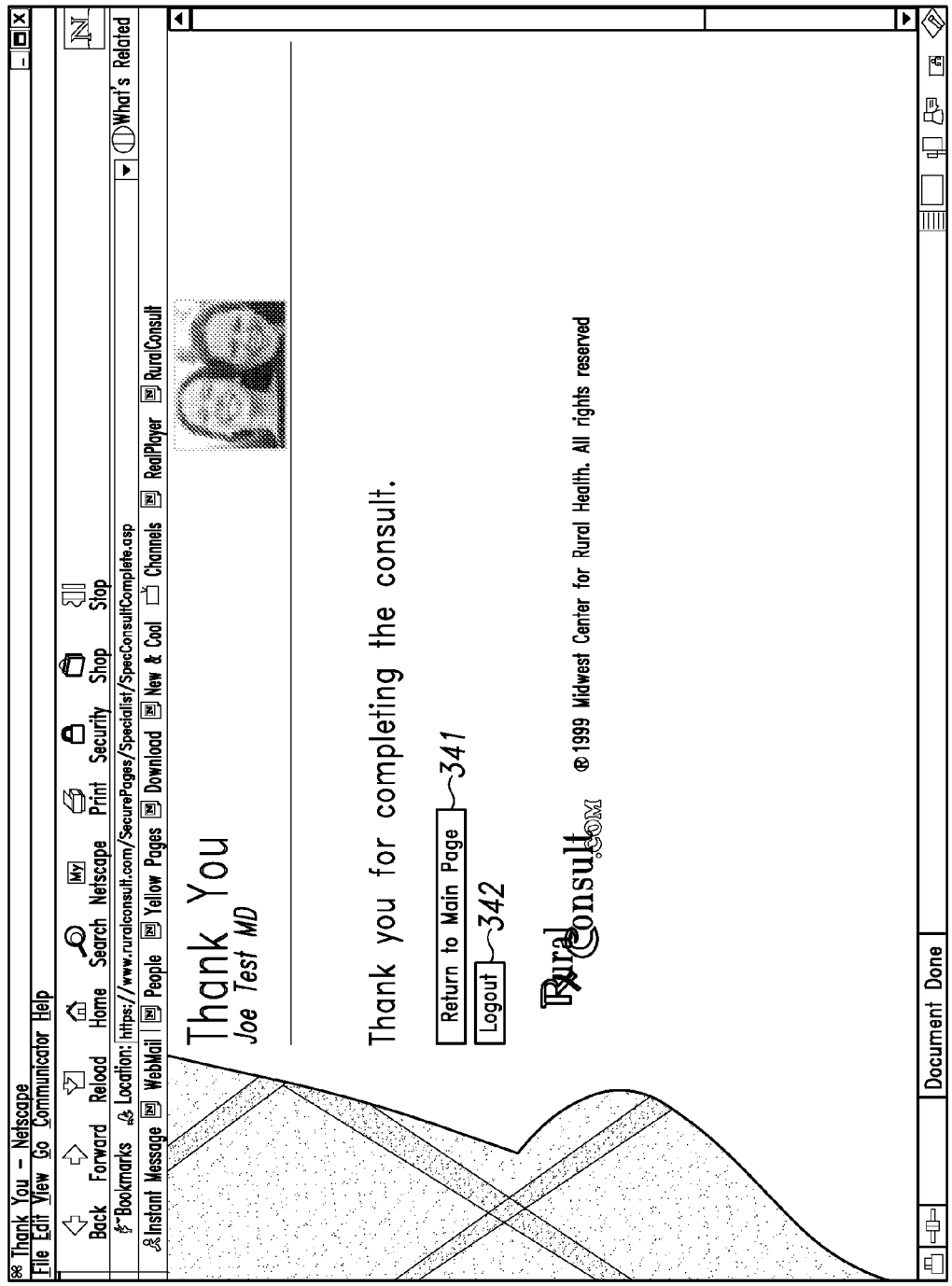
FIG. 27 illustrates a "thank you" page of an illustrative system according to the invention.

"Thank you" page 340, see FIG. 27, includes "return to main page" widget 341 and "logout" widget 342. If the health care provider selects the "return to main page" widget 341, server machine 20 responds with "select consult" page 300, FIG. 21. If the health care provider selects "logout" widget 342, server machine 20 responds with login page 110, FIG. 20.

Figure 23:
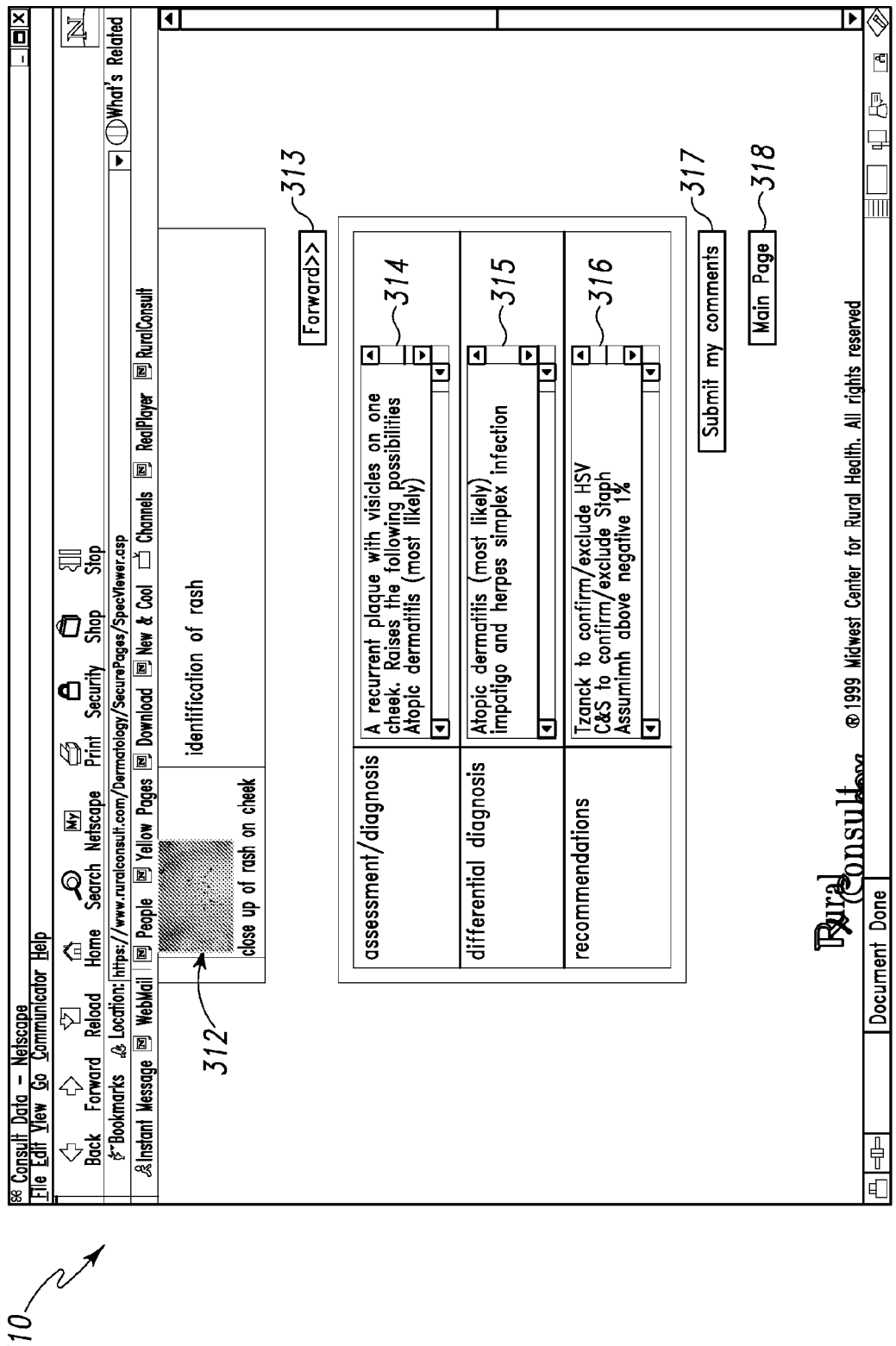
Figure 24:
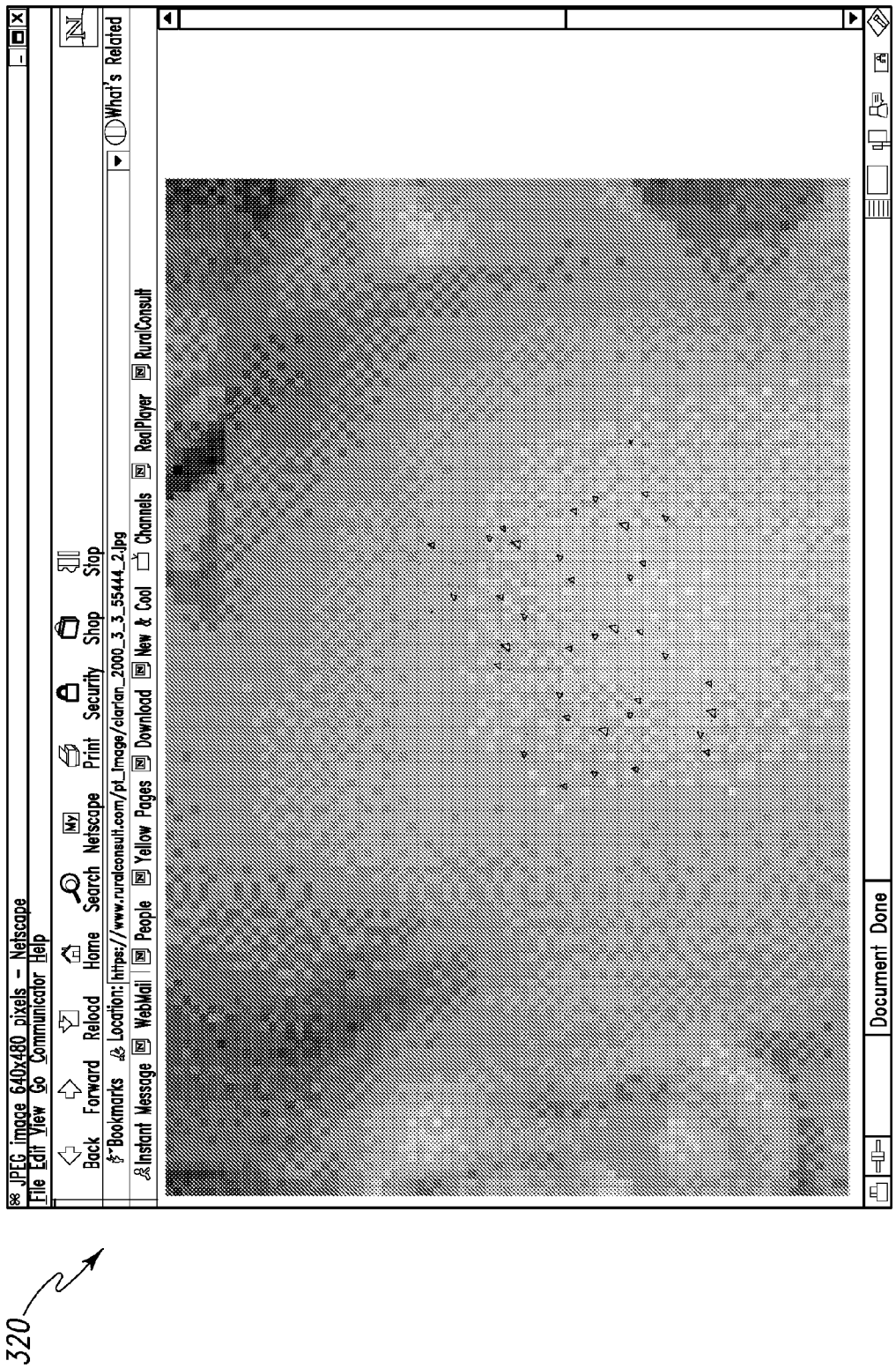

The completion of a consultation by a second health care provider is submitted by his or her selection of "submit my comments" widget 317 on "consult data" page 310, FIG. 23. Completion of a consultation by a second health care provider causes the server machine 20 to notify the first health care provider via email that the consultation is complete, and that the response to request for a consultation 70 is available for his review via the server machine 20.

Figure 29:
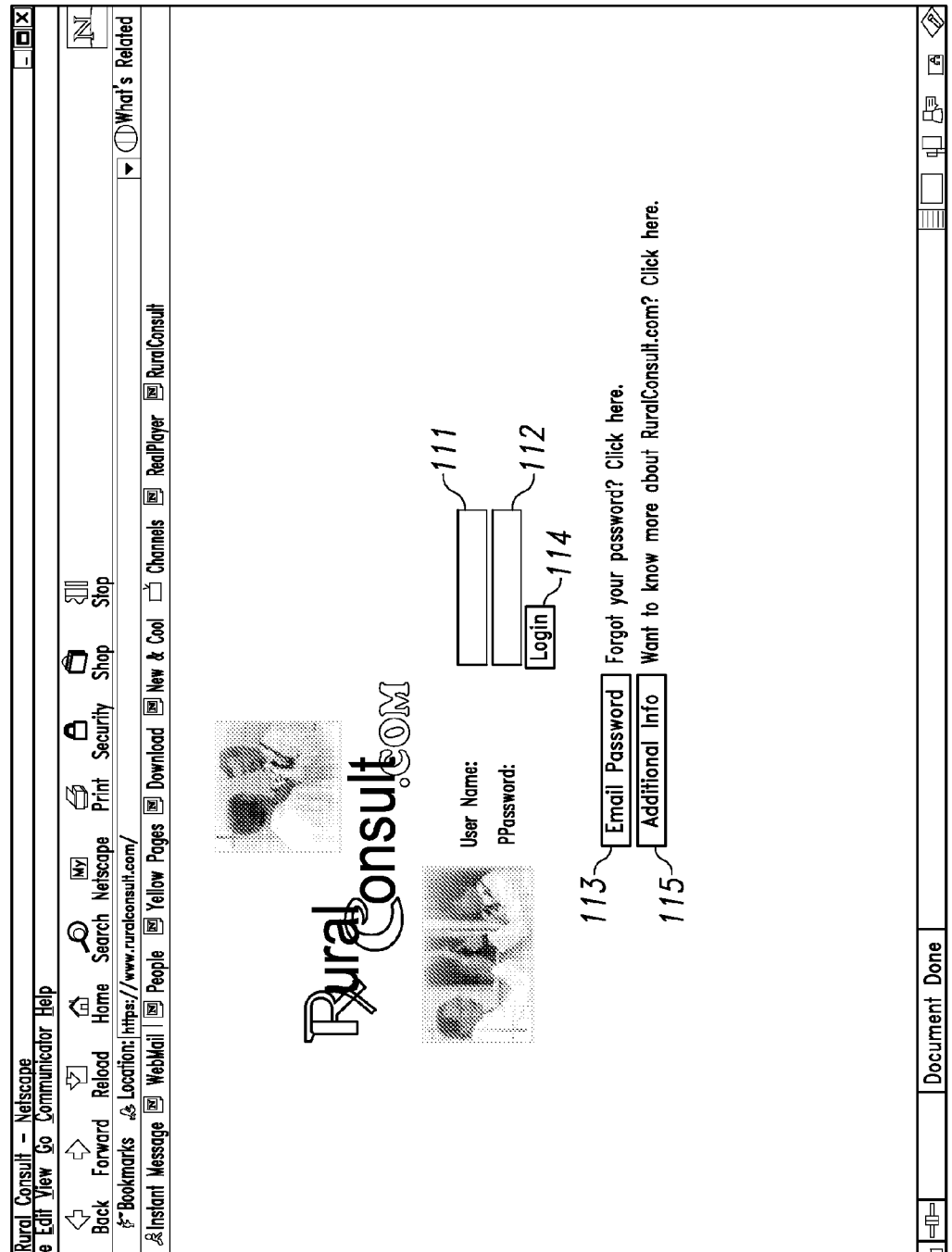
FIG. 29 illustrates a login page of an illustrative system according to the invention.

The first health care provider accesses the system a second time via the client machine 10 by providing the internet address of the server machine 20 to the web client software running on client machine 10. The server machine 20 responds with the login page 110, FIG. 29.

The login page 110 contains a "user name" widget 111, a "password" widget 112, an "email password" widget 113, a "login" widget 114 and an "additional info" widget 115. If the first health care provider desires additional information, he or she selects "additional info" widget 115, which causes the server machine 20 to display additional information about the system. If the first health care provider cannot remember his or her password, he or she selects "email password" widget 113, which causes the server machine 20 to e-mail his or her password to his or her registered e-mail address. The first health care provider retrieves the password and returns to home page 110.

Figure 30:
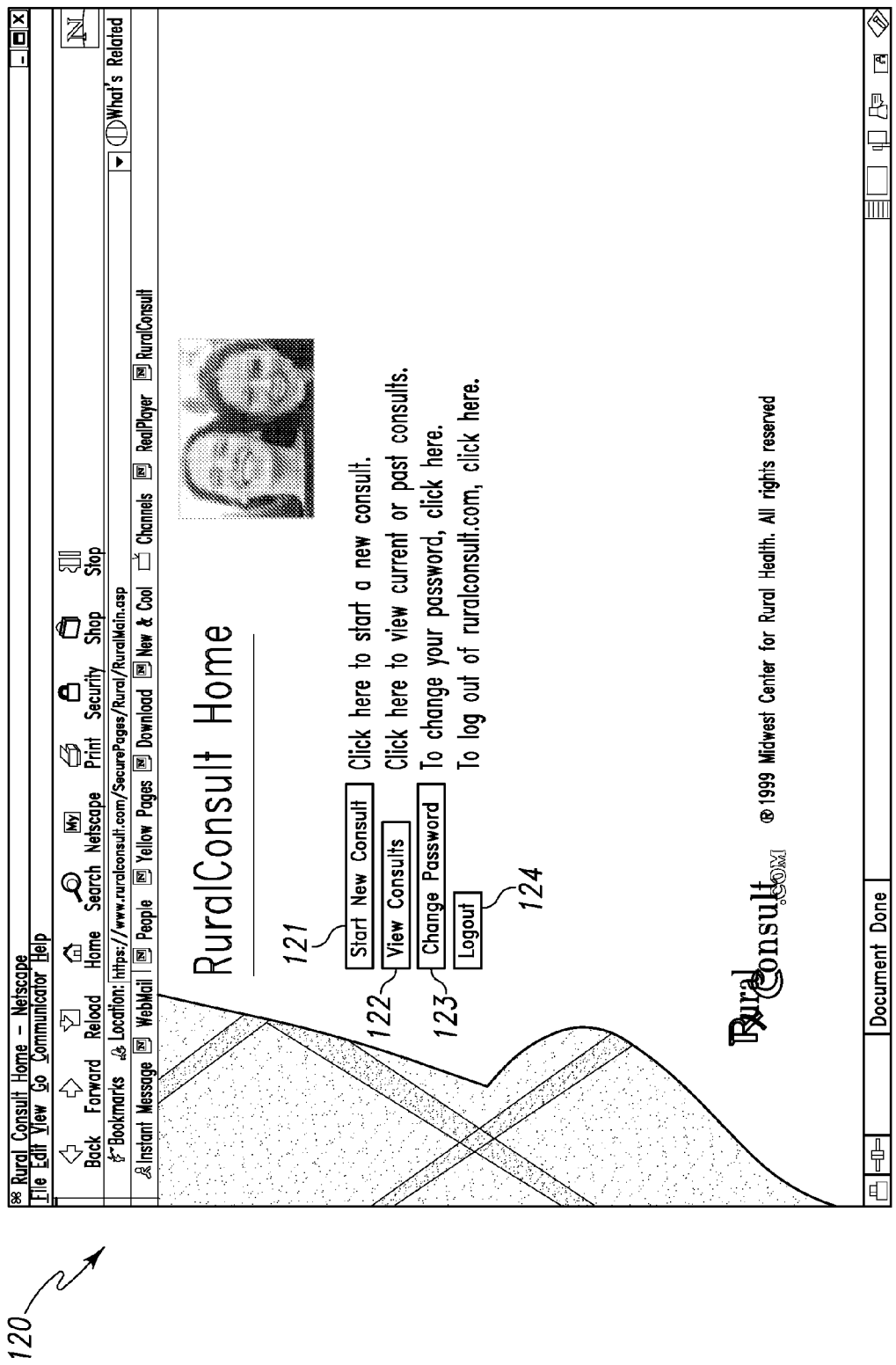
FIG. 30 illustrates a home page of an illustrative system according to the invention.

The first health care provider enters his or her user name into "user name" widget 111 of the login page 110 and his or her password into "password" widget 112 of the login page 110. The first health care provider selects "login" widget 114 The server machine 20 responds with home page 120. See FIG. 30. Home page 120 includes "start new consult" widget 121, "view consults" widget 122, "change password" widget 123, and "logout" widget 124.

Figure 31:
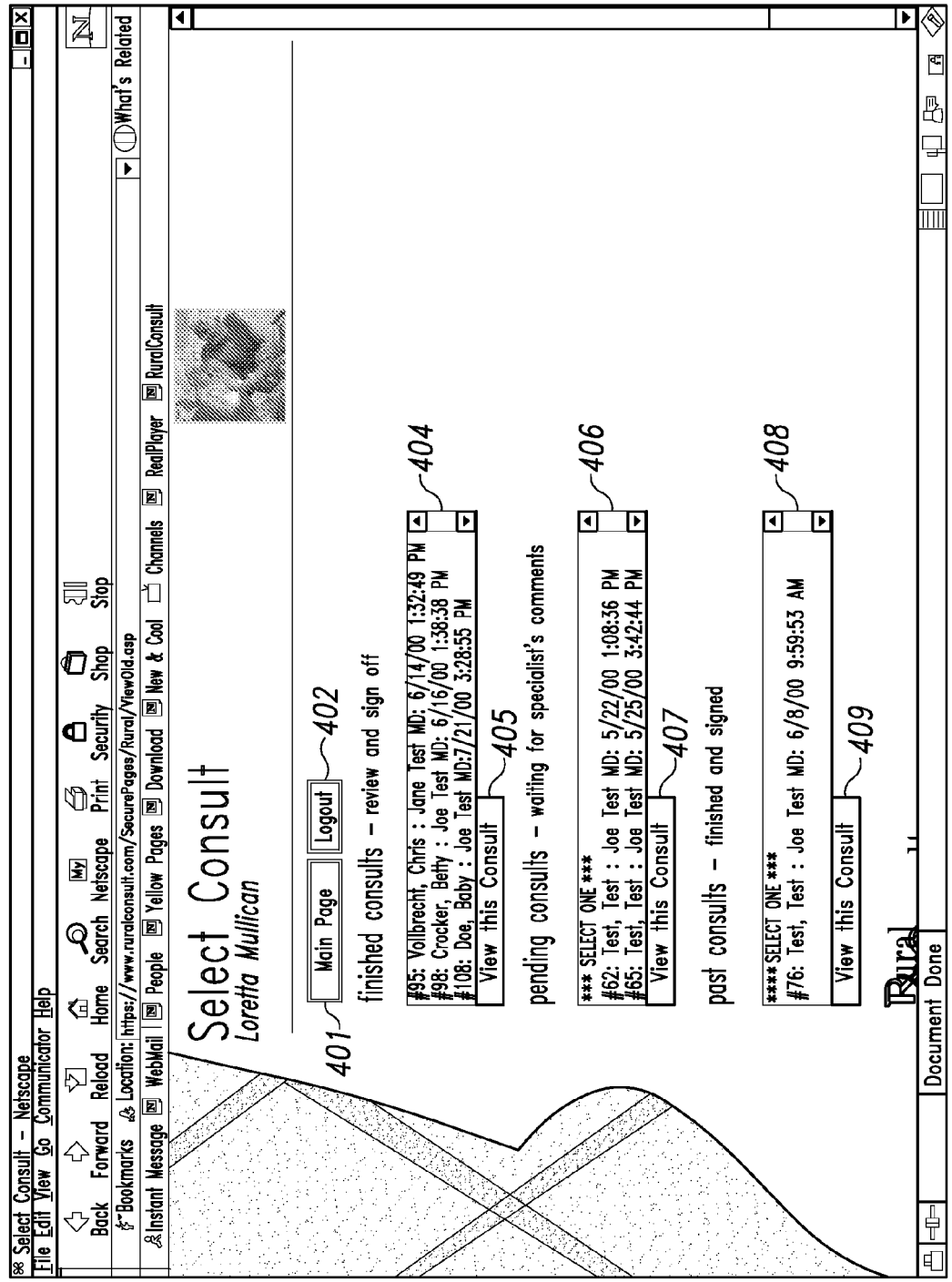
FIG. 31 illustrates a "select consult" page of an illustrative system according to the invention.

If the first health care provider selects "logout" widget 124, server machine 20 ends his or her session. If the health care provider selects "change password" widget 123, server machine 20 responds with a page which permits the health care provider to change his or her password. If health care provider selects "view consults" widget 122, server machine 20 responds with a "select consult" page 400. See FIG. 31.

"Select consult" page 400 includes a "main page" widget 401, a "logout" widget 402, "finished consults" list widget 404, a first "view this consult" widget 405, a "pending consults" list widget 406, a second "view this consult" widget 407, a "past consults" list widget 408, and a third "view this consult" widget 409. The first health care provider selects a consult from consult list widget 404, 406, or 408, and then selects the corresponding "view this consult" widget 405, 407, or 409.

Figure 32:
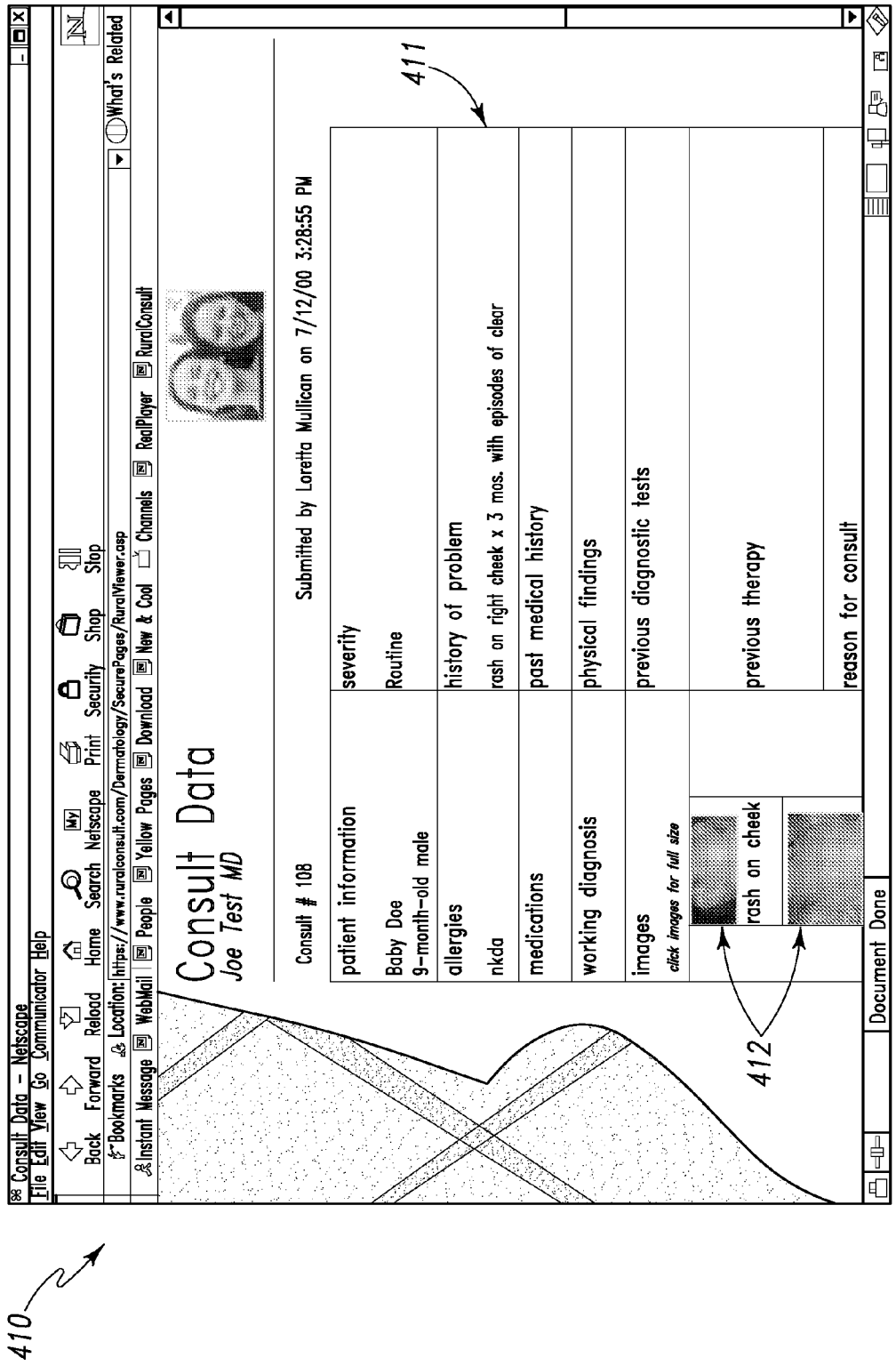
FIGS. 32-33 illustrate a "consult data" page of an illustrative system according to the invention.
Figure 33:
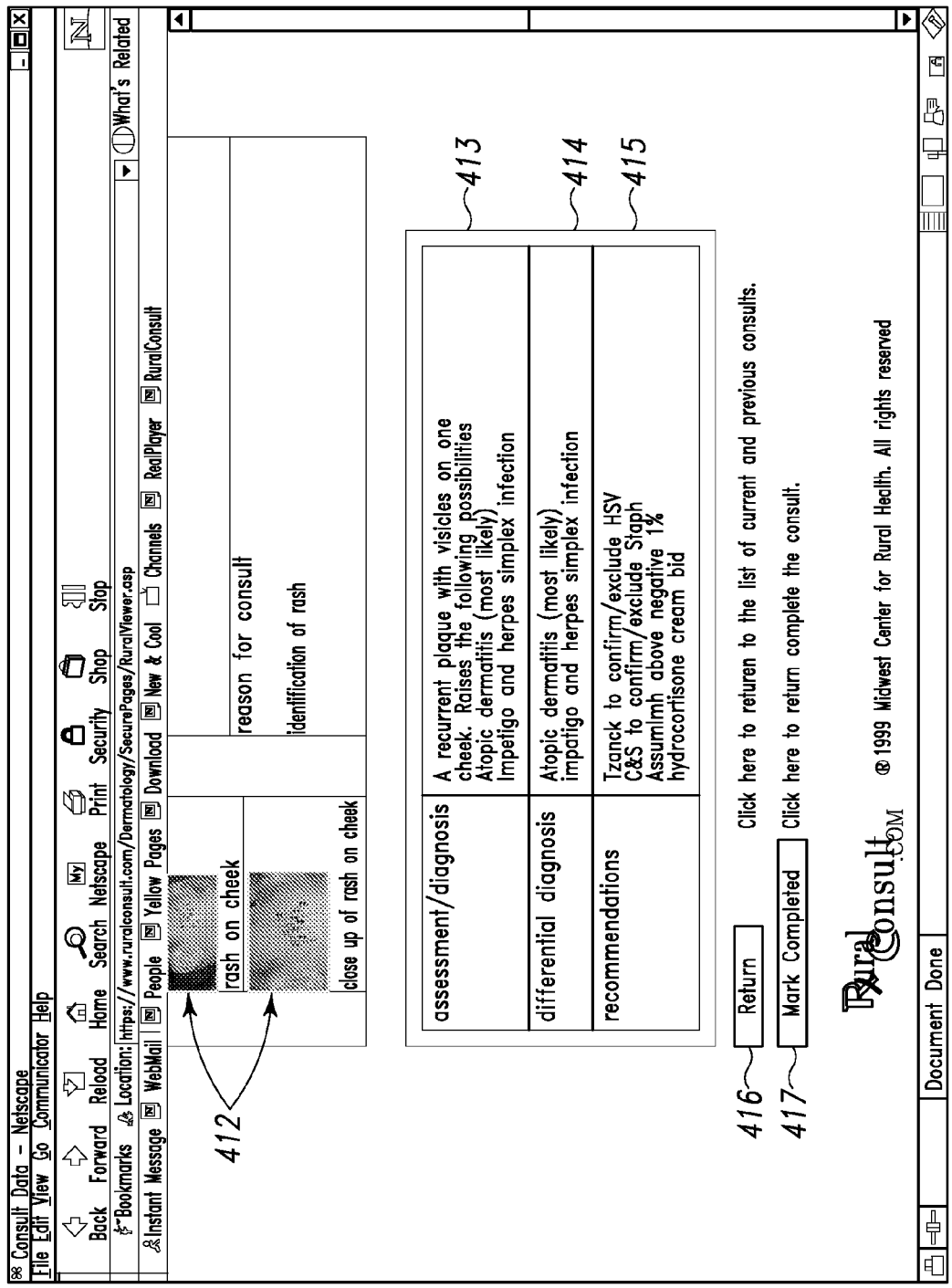

If the health care provider selects a finished consult from the "finished consults" list widget 404, and selects the "view this consult" widget 405, the server machine 20 responds with "consult data" page 410. See FIGS. 32-33.

Figure 34:
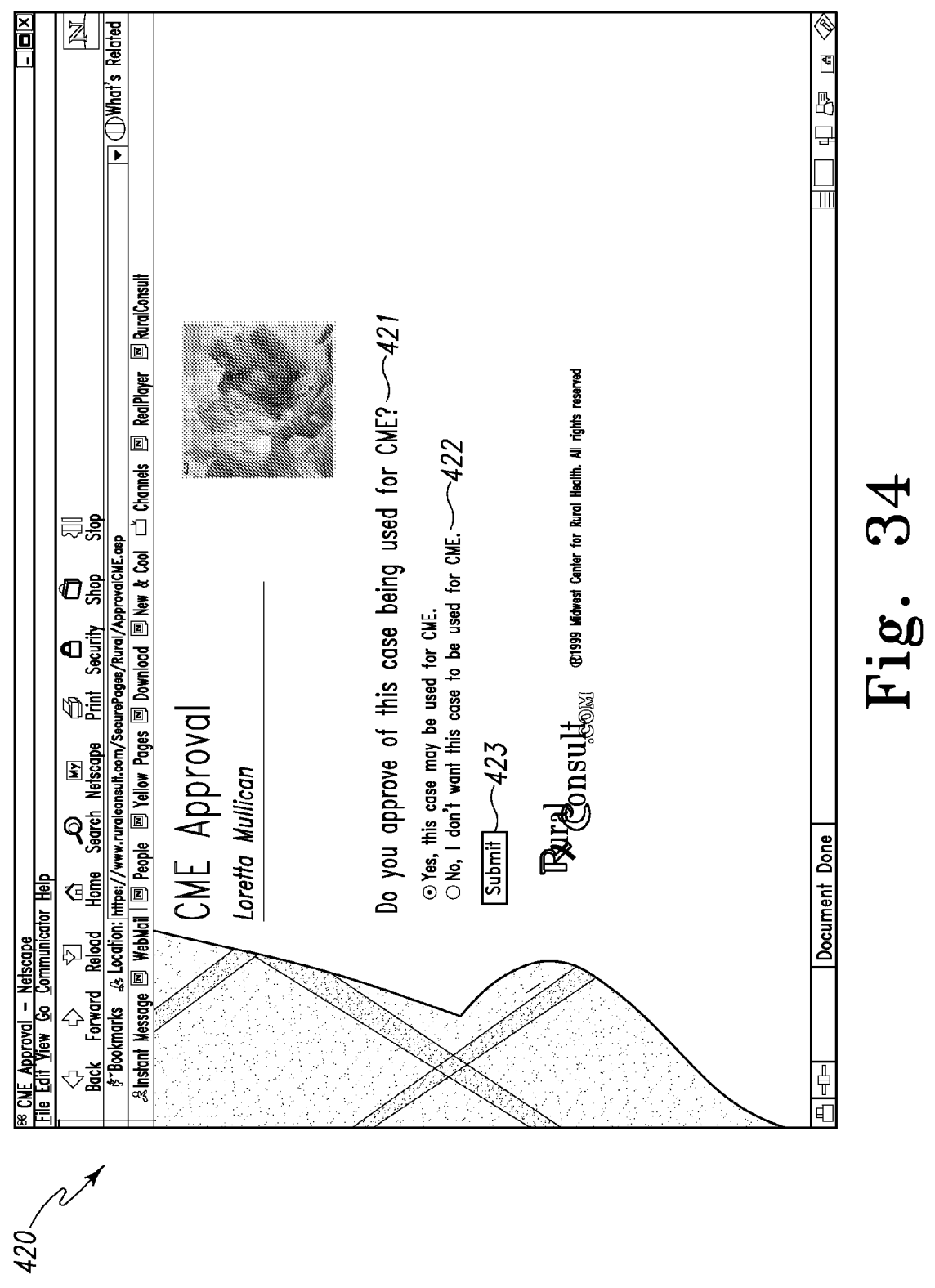

"Consult data" page 410 includes consult data form 411, "assessment/diagnosis" field 413, "differential diagnosis" field 414, "recommendations" field 415, "return" widget 416, and "mark completed" widget 417. Consult data form 411 includes thumbnail images 412. If the health care provider selects "return" widget 416, the server machine 20 responds with "select consult" page 400, FIG. 31. If the health care provider selects "mark completed" widget 417, the server machine 20 responds with a CME approval page 420. See FIG. 34.

"CME approval" page 420 includes a "yes, this case may be used for CME" radio button 421, a "no, I don't want this case to be used for CME" radio button 422, and a "submit" widget 423. The health care provider selects either the "yes" radio button 421 or the "no" radio button 422. The health care provider selects the "submit" widget 423, which causes the server machine 20 to respond with the "select consult" page 400, FIG. 31.

Figure 35:
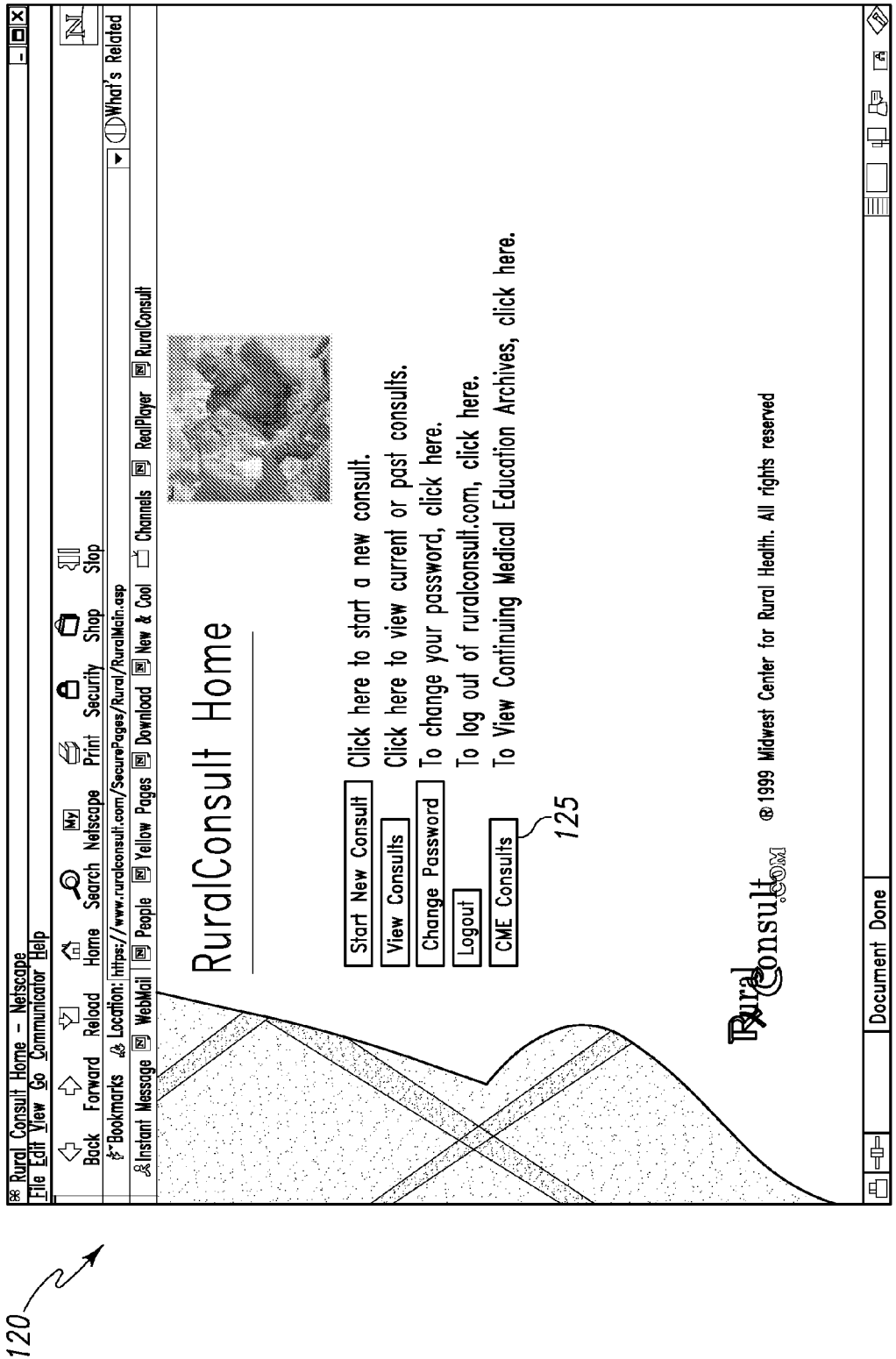
FIG. 35 illustrates a home page of another illustrative system according to the invention.
Figure 36:
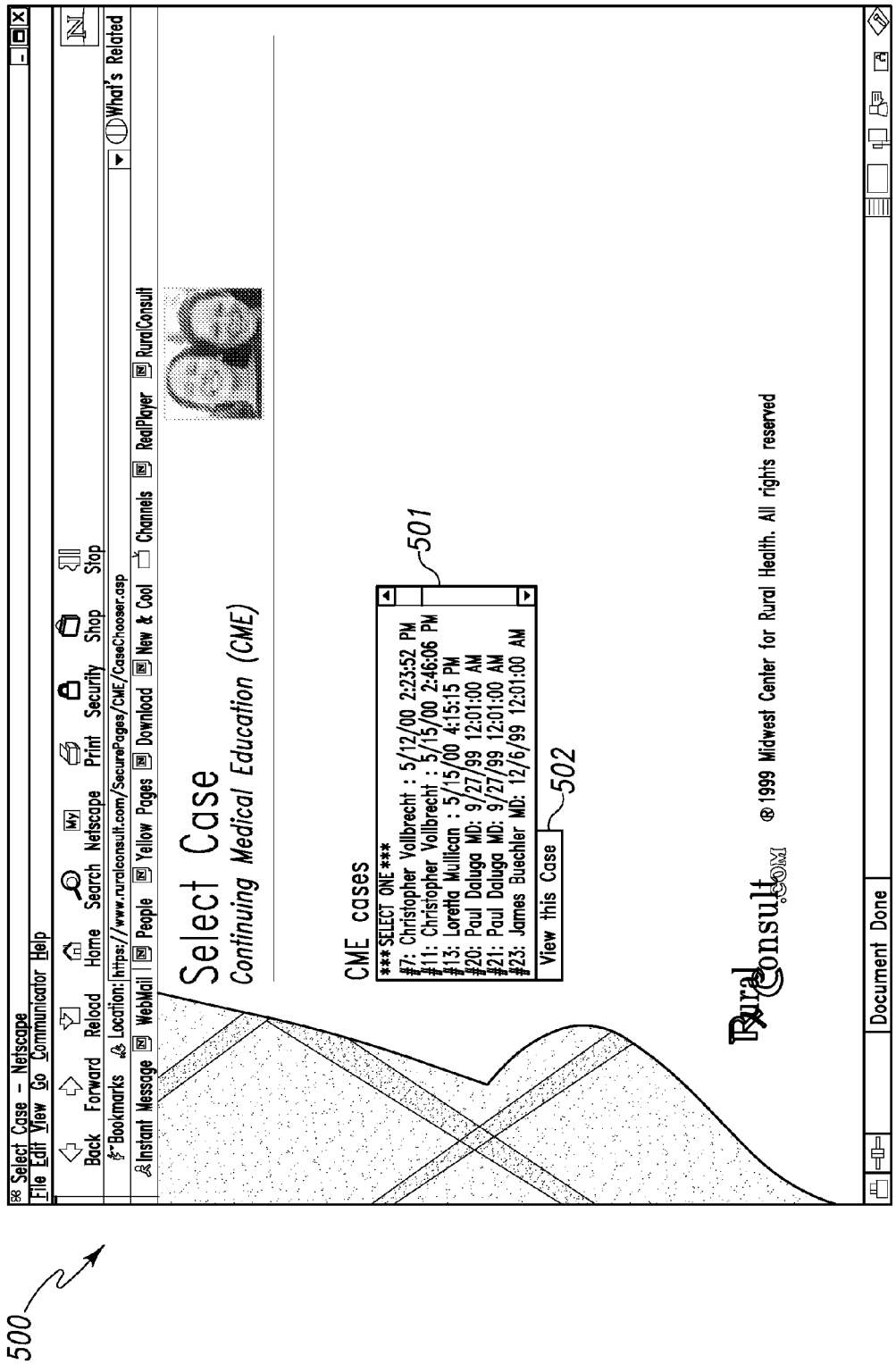
FIG. 36 illustrates a select case page of another illustrative system according to the invention; and, FIGS. 37-39 illustrate a "case data" page of another illustrative system according to the invention.
Figure 37:
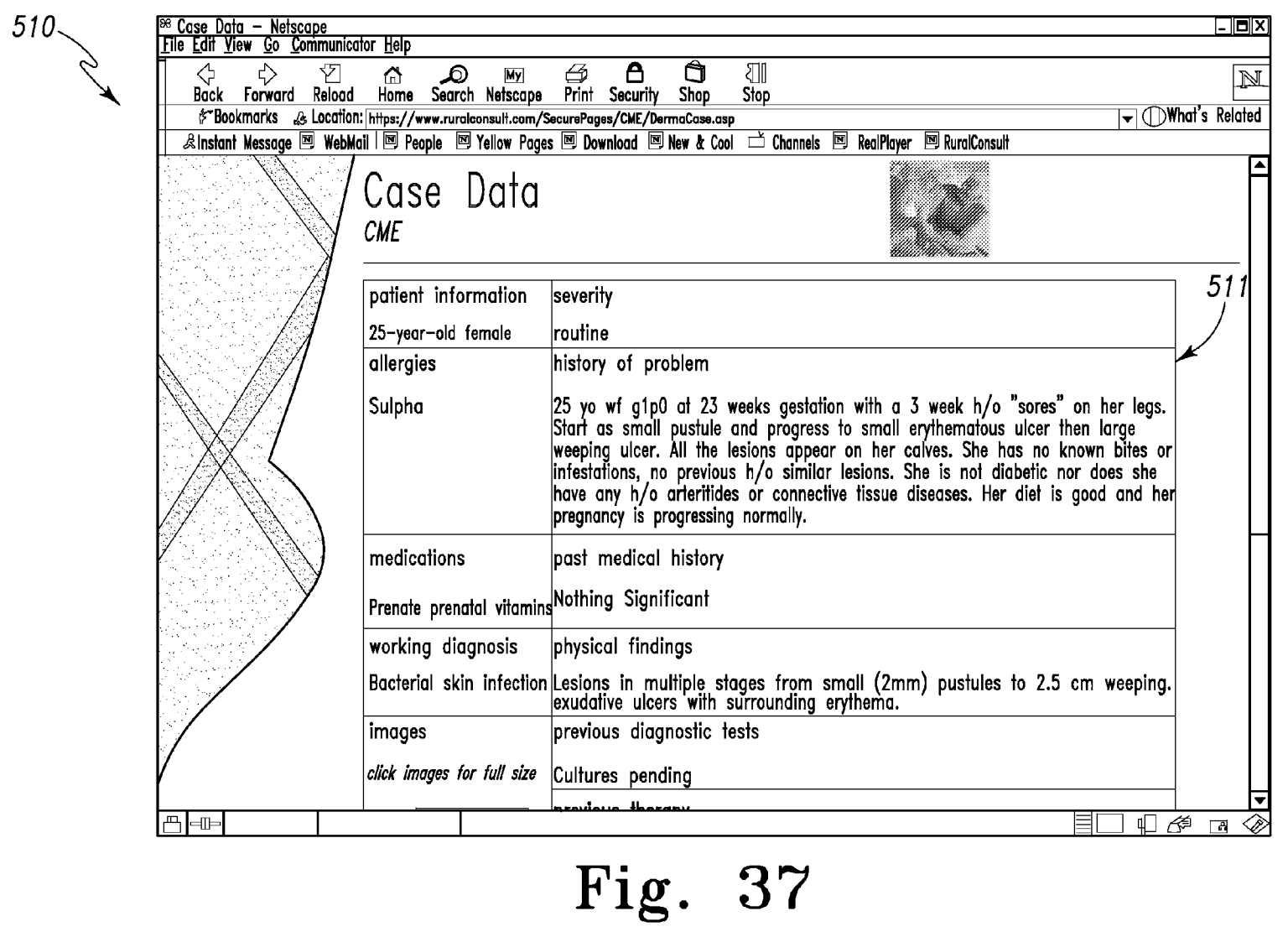

In another embodiment of the invention, a method is provided for healthcare providers to view CME consults. See FIG. 35. In this embodiment, the home page 120 includes a "CME consults" widget 125. If a health care provider selects "CME consults" widget 125 on the home page 120, the server 20 responds with a "select case" page 500. See FIG. 36. "Select case" page 500 includes a "CME cases" list widget 501, and a "view this case" widget 502. The health care provider selects one of the cases in the "CME cases" list widget 501, and selects the "view this case" widget 502. The server 20 responds with a "case data" page 510. See FIGS. 37-39.

Figure 38:
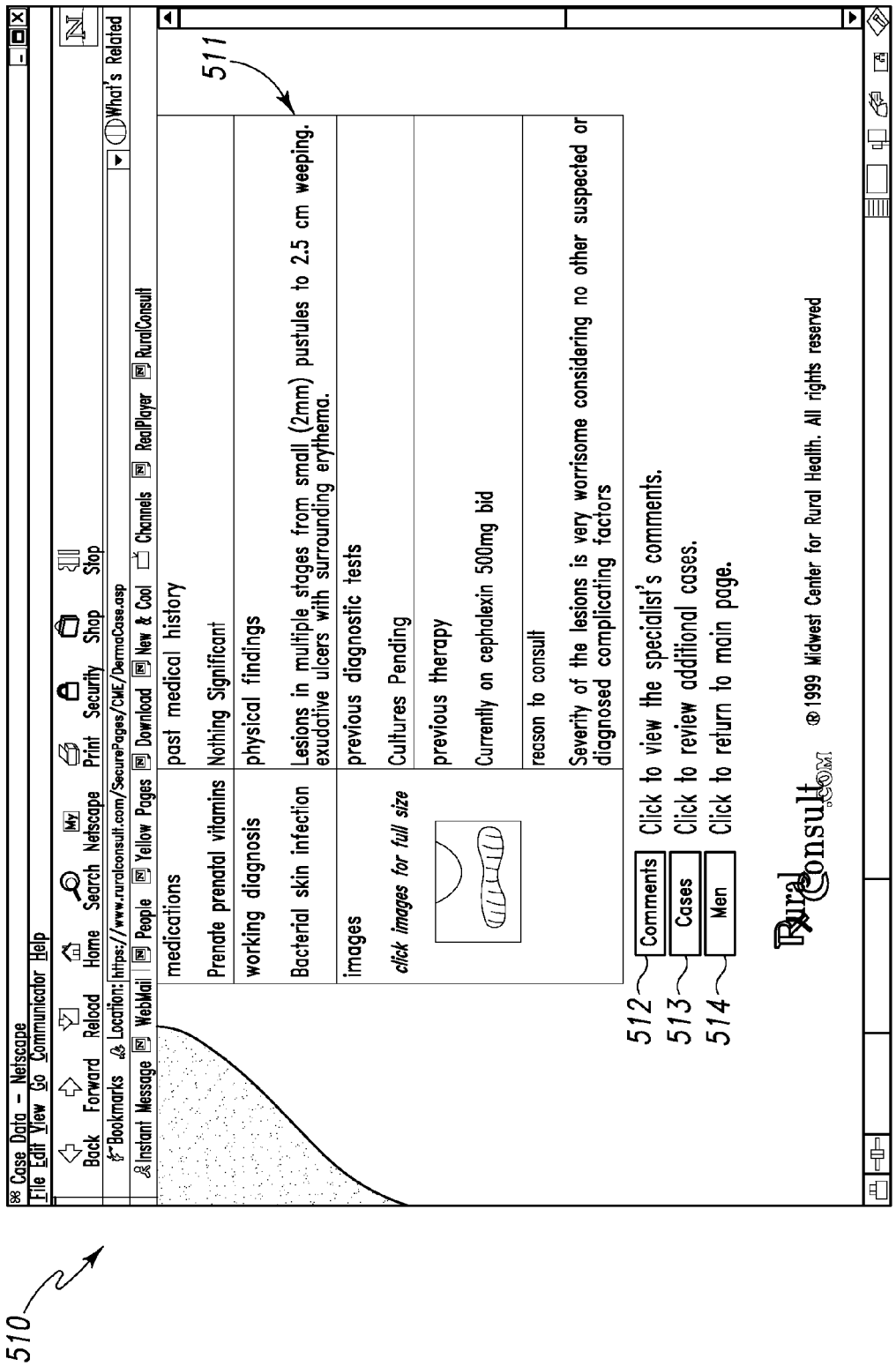

"Case data" page 510 includes a "patient information" form 511, a "comments" widget 512, FIG. 38, a "cases" widget 513, and a "main" widget 514. "Patient information" form 511 includes data fields containing the information entered by the original health care provider requesting a consult. If the health care provider selects "comments" widget 512, server 20 responds by appending the specialist's comments 515, FIG. 39, to the end of "patient information" form 511. Specialist's comments 515 include an "assessment/diagnosis" field 516, a "differential diagnosis" field 517, and a "recommendations" field 518. If the health care provider selects the "cases" widget 513, the server machine 20 responds with "select case" page 500, FIG. 36. If the health care provider selects "main" widget 514, server 20 responds with home page 120, FIG. 35.

Figure 7:
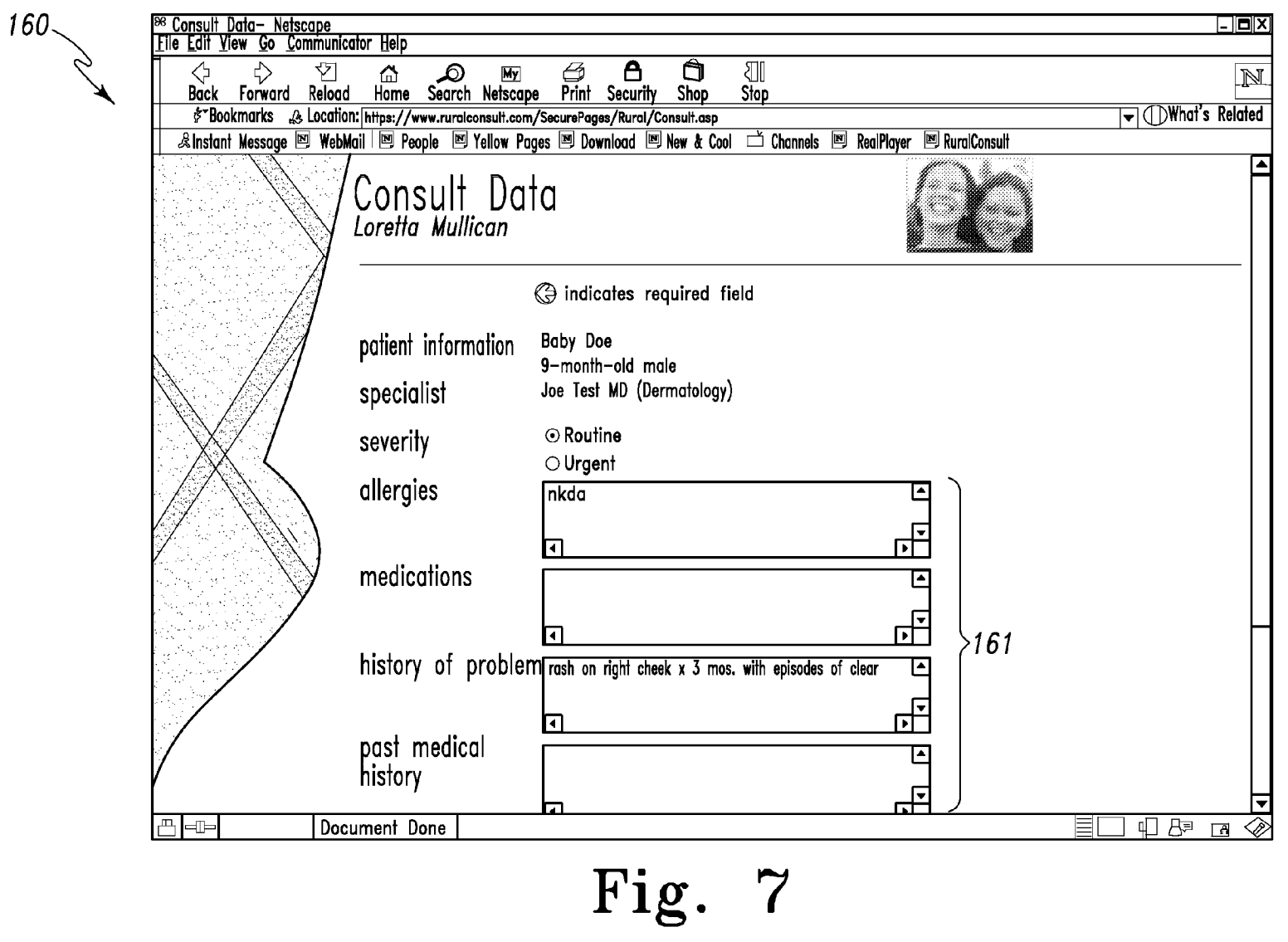
Figure 8:
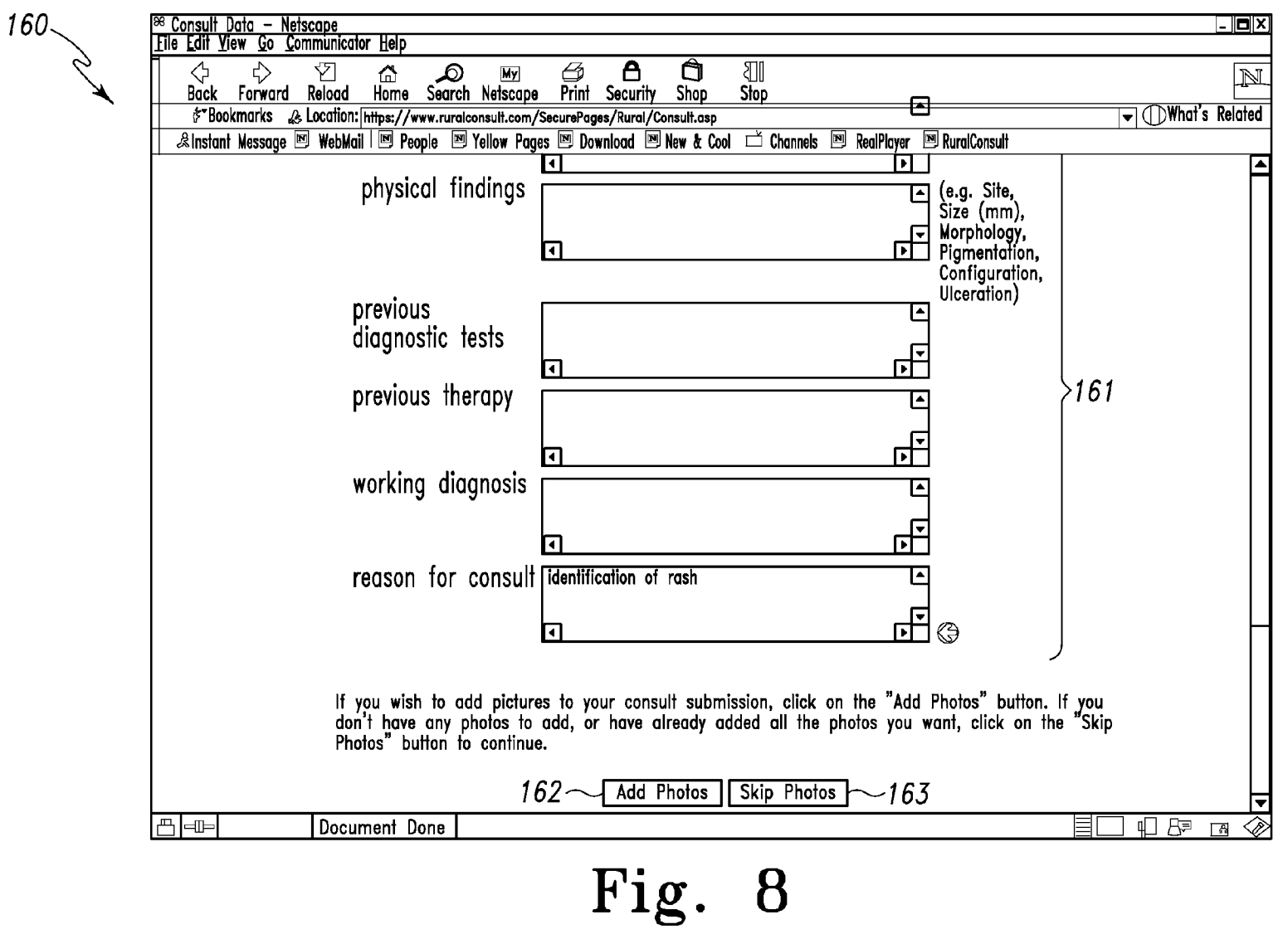

In another illustrative embodiment, "consult data" page 160, FIGS. 7-8, may contain additional widgets for adding movies, sounds, and other forms of digital media to convey diagnostic information. For example, an "add movie" widget can be located adjacent to "add photos" widget 162. The health care provider can select the "add movie" widget, and server 20 will respond with an "add movies to your consult" window similar to the "add images to your consult" window 170. Because computers store images, movies, sounds, three-dimensional models, and most other information as files, the disclosed method is capable of utilizing virtually any type of diagnostic data-containing file.

The advantages of the present invention will be clear from the foregoing description. However, a number of further variations can be made. For example, it is possible to include the server 20 software on one of the client machines 10, 30, so that only two computers are required. Furthermore, it is possible to include all software on one machine so that only one computer is required. Alternatively, in an environment servicing a large number of health care providers, it is possible to utilize multiple physical computers to host the server 20 software and the associated database. It is understood that many other variations can be made without departing from the scope of the present invention.

What is claimed is:

1. A method for a first healthcare provider to consult a second healthcare provider regarding at least one of diagnosis and treatment of a patient, the method comprising:

receiving a request for a consultation over a network submitted by the first healthcare provider via a first machine, the request including consult data;

storing the consult data in a database;

transmitting a notification over the network to the second healthcare provider in response to receiving the request for a consultation the notification informing the second healthcare provider that a request for a consultation has been received;

receiving a request for the consult data over the network from the second healthcare provider;

transmitting the consult data over the network to a second machine in response to the request for the consult data;

receiving a consultation over the network submitted by the second healthcare provider, the consultation including the second healthcare provider's assessment and/or diagnosis based on the consult data;

storing the consultation in the database;

transmitting a notification over the network to the first healthcare provider in response to receiving the consultation from the second healthcare provider, the notification informing the first healthcare provider that a consultation has been received;

receiving a request to view the consultation over the network from the first healthcare provider;

transmitting the consultation over the network to the first machine in response to the request to view the consultation;

transmitting a request for approval to use the consultation for medical educational purposes over the network to the first healthcare provider;

receiving an approval to use the consultation for medical educational purposes over the network from the first healthcare provider; and electronically identifying the consultation as usable for medical education purposes in response to the approval received from the first healthcare provider.

2. The method of claim 1, wherein the consult data includes at least one of textual queries and textual statements.

3. The method of claim 1, wherein the consult data includes at least one of still images and moving images.

4. The method of claim 1, wherein the consult data includes sounds.

5. The method of claim 1, wherein transmitting the notification over the network to the second healthcare provider comprises generating an e-mail to the second healthcare provider, the e-mail informing the second healthcare provider that a request for a consultation has been received.

6. The method of claim 1, wherein transmitting the notification over the network to the first healthcare provider comprises generating an e-mail to the first healthcare provider, the e-mail informing the first healthcare provider that a consultation has been received.

7. The method of claim 1, wherein storing the consultation in the database comprises storing at least one of textual queries and textual statements in the database.

8. The method of claim 1, wherein storing the consultation in the database comprises storing at least one of still images and moving images in the database.

9. The method of claim 1, wherein storing the consultation in the database comprises storing sounds in the database.

10. The method claim 1, further comprising:

receiving a request for medical education over a network submitted by a third healthcare provider via a third machine;

determining a number of consultations electronically identified as usable for medical educational purposes; and transmitting data over the network to the third machine, the data including a list of the consultations electronically identified as usable for medical educational purposes.

11. The method of claim 10, further comprising:

determining a selected consultation from the list of consultations electronically identified as usable for medical educational purposes based on a selection made by the third healthcare provider;

retrieving the selected consultation from the database; and transmitting the selected consultation over the network to the third machine.

12. The method of claim 1, further comprising electronically identifying the request for a consultation as pending until the second healthcare provider submits the consultation.

13. The method of claim 1, further comprising electronically identifying the request for a consultation as completed in response to receiving the consultation.

14. A method for a first healthcare provider to consult a second healthcare provider regarding at least one of diagnosis and treatment of a patient, the method comprising:

receiving a request for a consultation over a network submitted by the first healthcare provider via a first machine, the request including consult data;

storing the consult data in a database;

transmitting a notification over the network to the second healthcare provider in response to receiving the request for a consultation, the notification informing the second healthcare provider that a request for a consultation has been received;

receiving a request for the consult data over the network from the second healthcare provider;

transmitting the consult data over the network to a second machine in response to the request for the consult data;

receiving a consultation over the network submitted by the second healthcare provider, the consultation including the second healthcare provider's assessment and/or diagnosis based on the consult data;

transmitting a notification over the network to a third healthcare provider in response to receiving the request for a consultation, the notification informing the third healthcare provider that a request for a consultation has been received;

receiving a request for the consult data over the network from the third healthcare provider;

transmitting the consult data over the network to a third machine in response to the request for the consult data from the third healthcare provider; and receiving a consultation over the network submitted by the third healthcare provider, the consultation including the second healthcare provider's assessment and/or diagnosis based on the consult data.

15. The method of claim 14, further comprising:

storing the consultation submitted by the third healthcare provider in the database; and transmitting a notification over the network to the first healthcare provider in response to receiving the consultation submitted by the third healthcare provider, the notification informing the first healthcare provider that a consultation has been received.

16. The method of claim 15, wherein transmitting the notification over the network to the first healthcare provider in response to receiving the consultation submitted by the third healthcare provider comprises generating an e-mail to the first healthcare provider, the e-mail informing the first healthcare provider that a consultation has been received.

17. The method of claim 15, wherein storing the consultation submitted by the third healthcare provider comprises storing at least one of textual queries and textual statements in the database.

18. The method of claim 15, wherein storing the consultation submitted by the third healthcare provider comprises storing at least one of still images and moving images in the database.

19. The method of claim 15, wherein storing the consultation submitted by the third healthcare provider in the database comprises storing sounds in the database.

20. The method of claim 15, further comprising:

receiving a request to view the consultation submitted by the third healthcare provider over the network from the first healthcare provider; and transmitting the consultation submitted by the third healthcare provider over the network to the first machine in response to the request to view the consultation.

21. The method of claim 20, further comprising transmitting a request for approval to use the consultation submitted by the third healthcare provider for medical educational purposes over the network to the first healthcare provider.

22. The method of claim 21, further comprising:

receiving an approval to use the consultation submitted by the third healthcare provider for medical educational purposes over the network from the first healthcare provider; and electronically identifying the consultation submitted by the third healthcare provider as usable for medical education purposes in response to the approval received from the first healthcare provider.

* * * * *